US010808215B2

(12) United States Patent
Brutinel et al.

(10) Patent No.: US 10,808,215 B2
(45) Date of Patent: Oct. 20, 2020

(54) SELF-CONTAINED ANAEROBIC CULTURE DEVICE FOR SULFATE-REDUCING MICROORGANISMS

(71) Applicant: 3M INNOVATIVE PROPERTIES COMPANY, St. Paul, MN (US)

(72) Inventors: Evan D. Brutinel, Inver Grove Heights, MN (US); Jason W. Bjork, Cottage Grove, MN (US); Adam J. Stanenas, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 284 days.

(21) Appl. No.: 15/503,481

(22) PCT Filed: Aug. 19, 2015

(86) PCT No.: PCT/US2015/045795
§ 371 (c)(1),
(2) Date: Feb. 13, 2017

(87) PCT Pub. No.: WO2016/028839
PCT Pub. Date: Feb. 25, 2016

(65) Prior Publication Data
US 2017/0233691 A1    Aug. 17, 2017

Related U.S. Application Data

(60) Provisional application No. 62/187,293, filed on Jul. 1, 2015, provisional application No. 62/039,638, filed on Aug. 20, 2014.

(51) Int. Cl.
| C12M 1/14 | (2006.01) |
| C12Q 1/04 | (2006.01) |
| C12M 1/26 | (2006.01) |
| C12M 1/12 | (2006.01) |
| C12M 1/00 | (2006.01) |
| C12M 1/34 | (2006.01) |

(52) U.S. Cl.
CPC .............. *C12M 33/00* (2013.01); *C12M 1/14* (2013.01); *C12M 23/04* (2013.01); *C12M 23/20* (2013.01); *C12M 25/06* (2013.01); *C12M 37/04* (2013.01); *C12M 41/36* (2013.01); *C12Q 1/04* (2013.01)

(58) Field of Classification Search
None
See application file for complete search history.

(56) References Cited

U.S. PATENT DOCUMENTS

| 4,565,783 A | 1/1986 | Hansen et al. |
| 4,775,626 A * | 10/1988 | Armenta ............... C12M 23/08 435/189 |
| 5,089,413 A | 2/1992 | Nelson et al. |
| 5,116,748 A | 5/1992 | Takahashi et al. |
| 5,232,838 A | 8/1993 | Nelson et al. |
| 5,409,838 A | 4/1995 | Wickert |
| 5,601,998 A | 2/1997 | Mach et al. |
| 6,322,750 B1 | 11/2001 | Barclay |
| 6,531,281 B1 | 3/2003 | Magot et al. |
| 6,649,406 B1 * | 11/2003 | Williams ............... C12M 23/04 435/287.9 |
| 6,689,438 B2 | 2/2004 | Kennedy et al. |
| 2004/0101954 A1 | 5/2004 | Graessle et al. |
| 2004/0102903 A1 | 5/2004 | Graessle et al. |
| 2005/0239200 A1 * | 10/2005 | Beckwith ............... C12M 23/04 435/299.1 |

FOREIGN PATENT DOCUMENTS

| CA | 2176895 | 11/1996 |
| CN | 1696306 A | 11/2005 |
| CN | 102329851 B | 9/2012 |
| JP | 57-74094 | 5/1982 |
| JP | 4-8298 | 1/1992 |
| JP | 4-117300 | 4/1992 |
| JP | H05-13200 U | 2/1993 |
| JP | 07-75545 | 3/1995 |
| JP | 2007-124985 | 5/2007 |
| JP | 2008-29332 | 2/2008 |
| RU | 2408734 | 1/2011 |
| WO | WO 99/29831 | 6/1999 |

(Continued)

OTHER PUBLICATIONS

Tittsler ("Advantages of Peptone Iron Agar for the Routine Detection of Hydrogen Sulphide Production" American Journal of Public Health, vol. 27, 1240-1242, 1937) (Year: 1937).*

Kalaganov, V.A. et al.; Rapid Method for Determination Hydrogen Sulfide-producing Bacteria in Water-miscible cutting Fluids; Neftepererabotka I Neftekhimiya (Moscow, Russian Federaiont); vol. 10; 1988; pp. 18-19.

(Continued)

*Primary Examiner* — Robert J Yamasaki
*Assistant Examiner* — Charles Zoltan Constantine

(57) ABSTRACT

The present disclosure provides a culture device for enumerating colonies of sulfate-reducing microorganisms. The device includes a body having a waterproof base, a waterproof coversheet attached to the base, and a growth compartment disposed therebetween. The growth compartment has a perimeter and an opening. A portion of the perimeter is defined by a waterproof seal. The portion can include >50% of the perimeter. Disposed in the growth compartment are a dry cold water-soluble gelling agent, a dry culture medium selected to facilitate growth of a sulfate-reducing bacterium or indicator reagent for detecting hydrogen sulfide production by a sulfate-reducing bacterium, and a dry first oxygen-scavenging reagent.

20 Claims, 10 Drawing Sheets

(56) References Cited

FOREIGN PATENT DOCUMENTS

| | | |
|---|---|---|
| WO | WO 2000/03035 | 1/2000 |
| WO | WO 2003/052126 | 6/2003 |
| WO | WO 2005/024047 | 3/2005 |
| WO | WO 2007/084655 | 7/2007 |
| WO | WO 2009/108229 | 9/2009 |
| WO | WO 2011/082305 | 7/2011 |
| WO | WO 2011/151793 | 12/2011 |
| WO | WO 2012/094603 | 7/2012 |
| WO | WO 2013/029106 | 3/2013 |
| WO | WO 2014/042933 | 3/2014 |
| WO | WO 2014/054494 | 4/2014 |
| WO | WO 2014/085333 | 6/2014 |
| WO | WO 2015/061213 | 4/2015 |

OTHER PUBLICATIONS

Junichi Takeuchi et al., Methods of the determination of the number and the activity of sulfate-reducing bacteria, Japan Journal of Water Pollution Research, 1988, vol. 11, Issue 1, pp. 38-49.

* cited by examiner

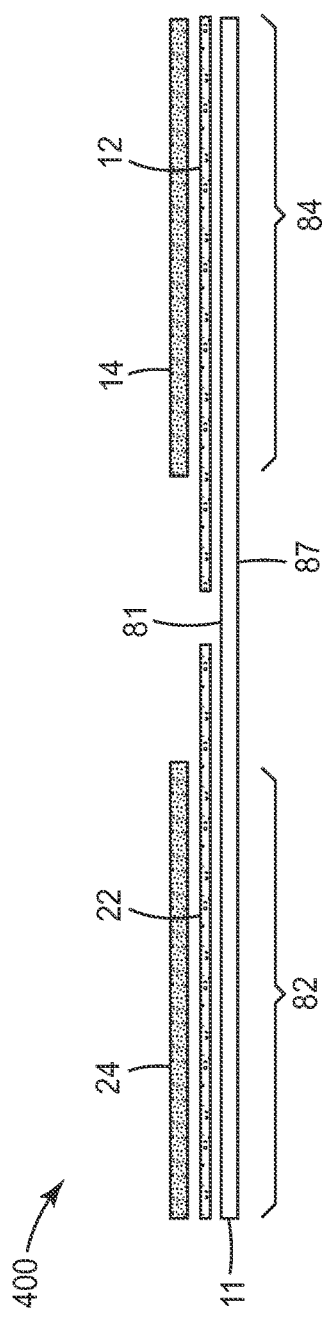
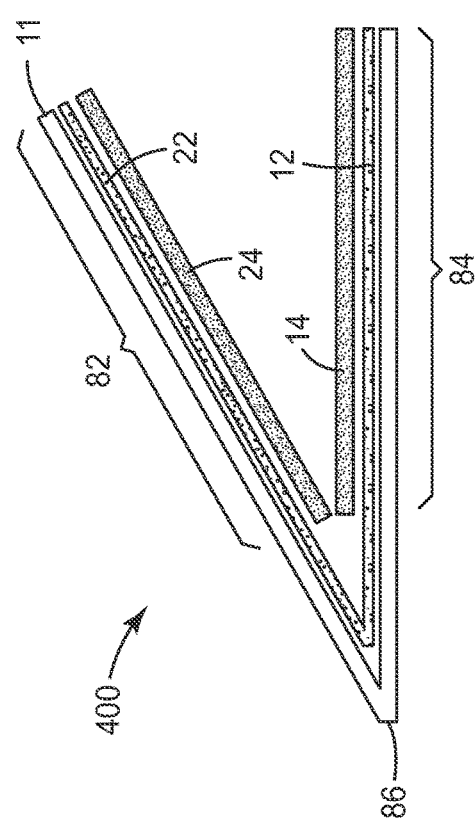
FIG. 7
FIG. 8

SELF-CONTAINED ANAEROBIC CULTURE DEVICE FOR SULFATE-REDUCING MICROORGANISMS

CROSS REFERENCE TO RELATED APPLICATIONS

This application is a national stage filing under 35 U.S.C. 371 of PCT/US2015/045795, filed Aug. 19, 2015, which claims the benefit of U.S. Provisional Patent Application Nos. 62/039,638, filed Aug. 20, 2014 and 62/187,293, filed Jul. 1, 2015, the disclosure of which are incorporated by reference in their entirety herein.

BACKGROUND

Sulfate-reducing bacteria (SRB) are ubiquitous in seawater, surface water that contains decaying organic matter, and in sediments found in marine and freshwater environments. SRB are commonly found in anaerobic environments, although it has been reported that at least some SRB may tolerate and reproduce in environments that have at least low levels of oxygen.

SRB obtain energy by oxidizing organic compounds or molecular hydrogen. They use sulfate as an electron acceptor to produce hydrogen sulfide ($H_2S$). Hydrogen sulfide production can contribute to corrosion of metals (e.g., metals that are used to produce pipes). This corrosion can result in disintegration of the metal and, ultimately, increased maintenance or failure of metal pipes. Biogenic sulfide can also cause corrosion of other materials such as concrete.

Methods for detection and enumeration of sulfate-reducing bacteria typically include preparation of anaerobic culture media and/or incubation of the culture media in an anaerobic atmosphere. Recently, nucleic acid amplification techniques have been used to detect SRB.

Although attempts have been made to develop a simple method for culturing SRB, there remains a need for improved methods for the enumeration of SRB.

SUMMARY

In general, the present disclosure relates to detection and, optionally, enumeration of sulfate-reducing microorganisms in a sample. In particular, the present disclosure relates to a device for culturing SRB in an aerobic atmosphere and methods of using the device. The growth and detection of SRB can be conducted using a self-contained, modified environment-generating culture device. The modified environment-generating device is activated with a predetermined volume of an aqueous liquid to produce an anaerobic aqueous growth medium that facilitates growth of SRB.

The inventive culture device and methods disclosed herein provide for growth, detection, and differentiation of sulfate-reducing microorganisms even while incubating the microorganisms in oxygen-containing (e.g., normal atmospheric oxygen-containing) environments. Advantageously, this eliminates the need for specialized incubation equipment and reagents (e.g., anaerobe jars, single-use anaerobe sachets, palladium catalysts, anaerobic glove boxes) that are typically required to culture sulfate-reducing microorganisms.

In one aspect, the present disclosure provides a culture device for enumerating colonies of sulfate-reducing microorganisms. The device can comprise a body comprising a waterproof base, a waterproof coversheet attached to the base, and a growth compartment disposed between the base and the coversheet. The growth compartment can have a perimeter and an opening that provides liquid access to the growth compartment. A portion of the perimeter is defined by a waterproof seal. The portion can include >50% of the perimeter. The device further can comprise a dry cold water-soluble gelling agent disposed in the growth compartment, a dry culture medium disposed in the growth compartment, and a dry first oxygen-scavenging reagent disposed in the growth compartment. The dry culture medium can be selected to facilitate growth of a sulfate-reducing bacterium. In any embodiment, the device optionally can comprise a dry indicator reagent for detecting hydrogen sulfide production by a sulfate-reducing bacterium, wherein the indicator reagent is disposed in the growth compartment.

In another aspect, the present disclosure provides a culture device for enumerating colonies of sulfate-reducing microorganisms. The device can comprise a body comprising a waterproof base, a waterproof coversheet attached to the base, and a growth compartment disposed between the base and the coversheet. The growth compartment can have a perimeter and an opening that provides liquid access to the growth compartment. A portion of the perimeter is defined by a waterproof seal. The portion can include >50% of the perimeter. The device further can comprise a dry cold water-soluble gelling agent disposed in the growth compartment, an indicator reagent disposed in the growth compartment, and a dry first oxygen-scavenging reagent disposed in the growth compartment. The indicator reagent can detect hydrogen sulfide production by a sulfate-reducing bacterium. In any embodiment, the device optionally can comprise a dry culture medium disposed in the growth compartment, wherein the indicator reagent is disposed in the growth compartment, wherein the dry culture medium is selected to facilitate growth of a sulfate-reducing bacterium.

In any of the above embodiments, the device further can comprise a carrier adhered to the base or the coversheet, wherein a portion of the carrier is disposed in the growth compartment.

In yet another aspect, the present disclosure provides a culture device for enumerating sulfate-reducing microorganisms. The device can comprise a body, a dry cold water-soluble gelling agent, a dry culture medium, and a dry first oxygen-scavenging reagent. The body can comprise a planar water-proof substrate. The substrate comprises a peripheral edge, a first major surface comprising spaced-apart first and second sections, a second major surface opposite the first major surface, and a fold that places a first section in overlapping juxtaposition with respect to the second section. The first section and the second section define inner walls of a growth compartment that comprises a perimeter and an opening that provides liquid access to the growth compartment. A portion of the perimeter is defined by a waterproof seal. The portion includes >50% of the perimeter. The cold water-soluble gelling agent can be adhered to the first section in the growth compartment. The dry culture medium can be disposed in the growth compartment and is selected to facilitate growth of a sulfate-reducing bacterium. The first oxygen-scavenging reagent can be disposed in the growth compartment.

In yet another aspect, the present disclosure provides a culture device for enumerating sulfate-reducing microorganisms. The device can comprise a body, a dry cold water-soluble gelling agent, an indicator reagent for detecting hydrogen sulfide production by a sulfate-reducing bacterium, and a dry first oxygen-scavenging reagent. The body can comprise a planar water-proof substrate. The substrate comprises a peripheral edge, a first major surface comprising spaced-apart first and second sections, a second major surface opposite the first major surface, and a fold that places a first section in overlapping juxtaposition with respect to the second section. The first section and the second section define inner walls of a growth compartment that comprises a perimeter and an opening that provides liquid access to the growth compartment. A portion of the perimeter is defined by a waterproof seal. The portion includes >50% of the perimeter. The cold water-soluble gelling agent can be adhered to the first section in the growth compartment. The indicator reagent can be disposed in the growth compartment. The first oxygen-scavenging reagent can be disposed in the growth compartment.

In any of the above embodiments, the cold water-soluble gelling agent can comprise hydroxypropyl methylcellulose. In any of the above embodiments, the first oxygen-scavenging reagent can be selected from the group consisting of ferric ammonium sulfate, ferric chloride, ferric iron salts, sulfite salts, bisulfite salts.

In yet another aspect, the present disclosure provides a method for detecting or enumerating sulfate-reducing microorganisms. The method can comprise depositing a sample into a growth compartment of a device, incubating the device at a temperature that facilitates growth of a sulfate-reducing microorganism, and detecting an indication of a colony of the sulfate-reducing microorganism in the growth compartment. The device can comprise a body comprising the growth compartment disposed between a waterproof base and a waterproof coversheet attached to the base, a dry cold water-soluble gelling agent adhered to the base in the growth compartment, and a dry first oxygen-scavenging reagent disposed in the growth compartment. The growth compartment can have a perimeter and an opening that provides liquid access to the growth compartment. A portion of the perimeter is defined by a waterproof seal, wherein the portion includes >50% of the perimeter.

In yet another aspect, the present disclosure provides a method for detecting or enumerating sulfate-reducing microorganisms. The method can comprise depositing a sample into a growth compartment of a device, incubating the device at a temperature that facilitates growth of a sulfate-reducing microorganism, and detecting an indication of a colony of the sulfate-reducing microorganism in the growth compartment. The body can comprise a planar water-proof substrate. The substrate comprises a peripheral edge, a first major surface comprising spaced-apart first and second sections, a second major surface opposite the first major surface, and a fold that places a first section in overlapping juxtaposition with respect to the second section. The first section and the second section define inner walls of a growth compartment that comprises a perimeter and an opening that provides liquid access to the growth compartment. A portion of the perimeter is defined by a waterproof seal. The portion includes >50% of the perimeter. The cold water-soluble gelling agent can be adhered to the first section in the growth compartment. The indicator reagent can be disposed in the growth compartment. The first oxygen-scavenging reagent can be disposed in the growth compartment.

In any of the above embodiments of the methods, prior to depositing the sample into the growth compartment, the growth compartment can contain a dry culture medium, the culture medium selected to facilitate growth of a sulfate-reducing bacterium. In any of the above embodiments of the methods, prior to depositing the sample into the growth compartment, the growth compartment can contain an indicator reagent for detecting hydrogen sulfide production by a sulfate-reducing bacterium. In any of the above embodiments of the methods, depositing the sample into the growth compartment further can comprise depositing an aqueous liquid into the growth compartment. In any of the above embodiments of the methods, the method further can comprise sealing the opening.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a nutrient can be interpreted to mean "one or more" nutrients.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The term "microorganism" or "microbe" as used herein refers to any microscopic organism, which may be a single cell or multicellular organism. The term is generally used to refer to any prokaryotic or eukaryotic microscopic organism capable of growing and reproducing in a suitable culture medium, including without limitation, one or more of bacteria. Microorganisms encompassed by the scope of the present invention include prokaryotes, namely the bacteria and archaea; and various forms of eukaryotes, comprising the protozoa, fungi, yeast (e.g., anaerobic yeast), algae etc. The term "target microorganism" refers any microorganism that is desired to be detected.

The term "anaerobic microorganism" or "anaerobe" as used herein refers to microorganisms which are sensitive to oxygen and will not grow in the presence of oxygen. An anaerobic microorganism or anaerobe is any organism that does not require oxygen for growth. Anaerobic microorganisms include both obligate anaerobes and facultative anaerobes. Obligate anaerobes are those microorganisms which will die when exposed to atmospheric levels of oxygen. A facultative anaerobe is an organism that can carry out aerobic respiration if oxygen is present, but is capable of switching to fermentation or anaerobic respiration if oxygen is absent. Methods and systems of the present invention could be used for the enrichment and detection of both obligate anaerobes and facultative anaerobes.

The term "culture" or "growth" of microorganisms as used herein refers to the method of multiplying microbial organisms by letting them reproduce in predetermined culture media under conditions conducive for their growth. More particularly it is the method of providing a suitable culture medium and conditions to facilitate at least one cell division of a microorganism. Culture media are solid, semi-solid or liquid media containing all of the nutrients and necessary physical growth parameters necessary for microbial growth.

The term "enrichment" as used herein refers to the culture method of selectively enriching the growth of a specific microorganism by providing medium and conditions with specific and known attributes that favors the growth of that particular microorganism. The enrichment culture's environment will positively influence the growth of a selected microorganism and/or negatively influence the growth of other microorganisms.

"Oxygen scavenging reagent" and "oxygen scavenger" will be used broadly herein to refer to a compound that can consume, deplete or react with oxygen from a given environment. Preferably, the oxygen scavenging reagent does not slow or inhibit growth of anaerobic microorganisms.

The term "reducing agent" refers to a substance that is capable of lowering the $E_h$ potential of the semisolid culture medium formed by hydration of the dry components in the growth compartment of a device of the present disclosure.

The term "carbon source", as used herein, refers to a substance that can be metabolized by a microorganism such that at least a portion of the carbon atoms in the carbon source are converted into biomass by the microorganism.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

FIGS. 6-9 are various views of a culture device comprising a unitary base according to the present disclosure.

DETAILED DESCRIPTION

Figure 1A:
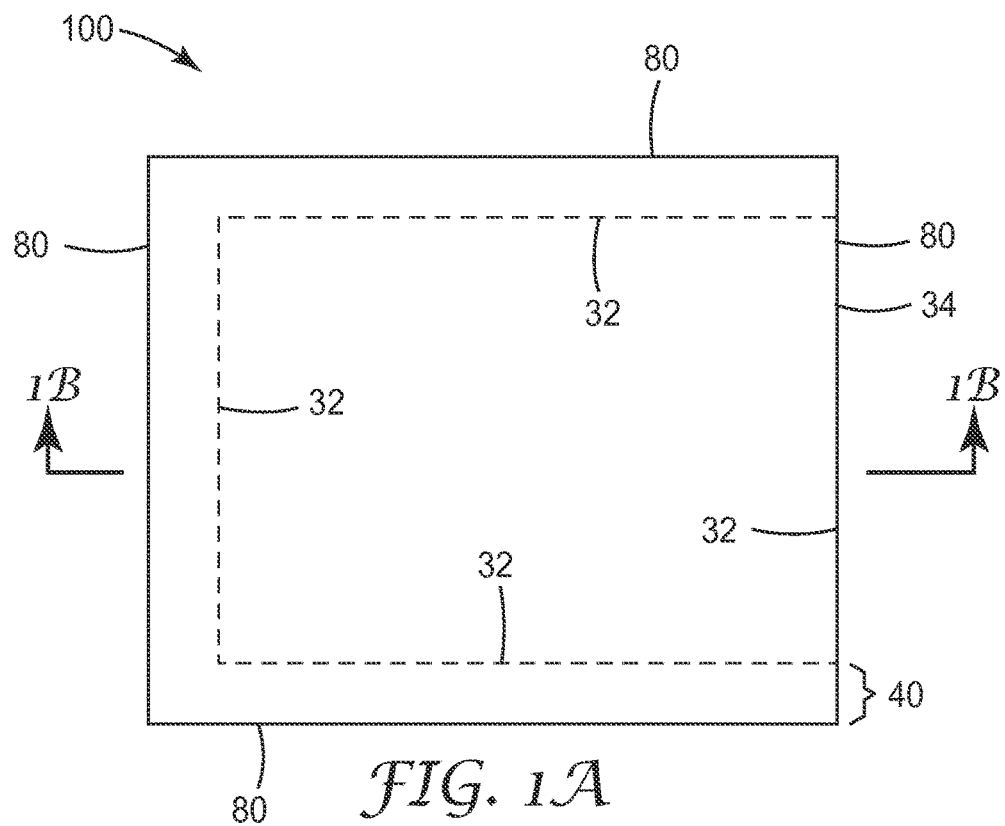
FIG. 1A is a plan view of one embodiment of a culture device according to the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to detection and, optionally, enumeration of sulfate-reducing microorganisms in a sample. For example, in some embodiments, the present disclosure relates to growth and detection of sulfate-reducing bacteria (SRB). The diverse group of SRB typically grown in anaerobic environments. It is now known that growth and detection of obligately-anaerobic sulfate-reducing microorganisms can be conducted using a self-contained reduced-oxygen environment-generating culture device that obviates the need for incubating the device itself in an anaerobic environment. Advantageously, in any embodiment, a device of the present disclosure distinguishes sulfate-reducing bacteria from bacteria that reduce other forms of oxidized sulfur compounds (e.g., bisulfite).

It is now known that a dry, rehydratable self-contained reduced-oxygen environment-generating culture devices can be made. The culture device comprises an effective amount of a substantially-dry oxygen-scavenging reagent disposed in a growth compartment of the culture device and being capable of rehydration in a predetermined volume of aqueous solution wherein, upon rehydration, the oxygen-scavenging reagent is capable of participating in an oxygen-consuming reaction. Further, it is now known the oxygen-consuming reaction can consume enough oxygen to facilitate growth of a microaerotolerant microorganism, a microaerophilic microorganism, or an obligately-anaerobic sulfate-reducing microorganism. Moreover, the culture device can be held in an aerobic environment during incubation wherein the culture device can maintain a reduced oxygen environment for up to about eight days in order to facilitate growth of the aforementioned microorganisms.

Bacterial species of interest can be analyzed in a test sample that may be derived from any source, such as a sample containing marine water, surface water (e.g., from ponds, lakes or rivers), or sediment from marine or freshwater-sources. In addition, the test sample may be obtained from oil deposits, oil wells, pipelines used to transport oil, or vessels used for storing oil.

Sulfate-reducing bacteria are ubiquitous in nature. These bacteria can be obligately-anaerobic or may be aerotolerant. Nonlimiting examples of obligately-anaerobic, sulfate-reducing bacteria include *Desulfovibrio* spp. and *Desulfotomaculum* spp.

Figure 1B:
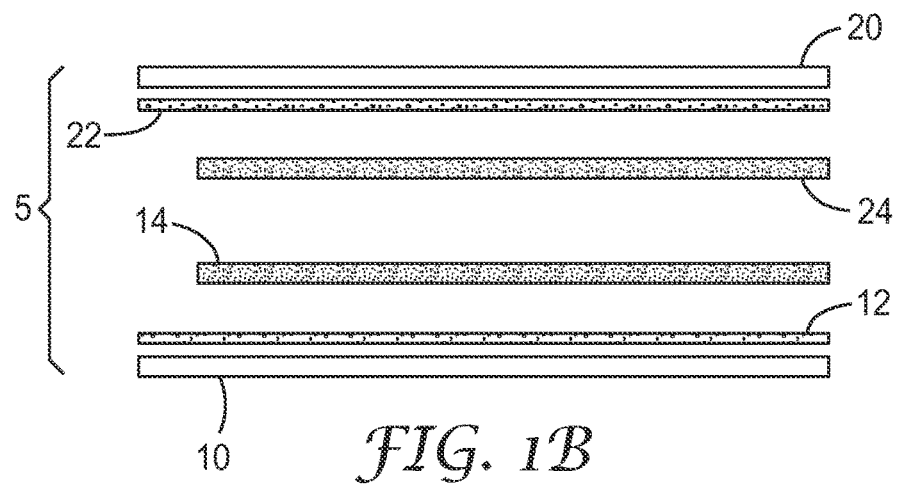
FIG. 1B is an exploded cross-sectional side view, along line 1B-1B, of the culture device of FIG. 1A.

In one aspect, the present disclosure provides a culture device for culturing and detecting a sulfate-reducing microorganism that grows in reduced-oxygen environments. With reference to FIGS. 1A and 1B, a culture device 100 of the present disclosure comprises a body 5 that includes a waterproof base 10, a waterproof coversheet 20, and a growth compartment 30 disposed between the base 10 and coversheet 20. The base 10 has an inner surface and an outer surface opposite the inner surface. The coversheet 20 has an inner surface and an outer surface opposite the inner surface. In any embodiment, the inner surface of the base 10 is disposed in facing relationship with the inner surface of the coversheet 20.

The growth compartment 30 has a perimeter 32 that includes an opening 34. The opening 34 provides liquid access to the growth compartment 30. A portion of the perimeter is defined by a waterproof seal 40. In any embodiment, the portion includes >50% of the perimeter 32 of the growth compartment 30. In any embodiment, the portion includes ≥80% of the perimeter 32 of the growth compartment 30. In any embodiment, the portion includes ≥90% of the perimeter 32 of the growth compartment 30. In any embodiment, the portion includes ≥95% of the perimeter 32 of the growth compartment 30. In any embodiment, the portion includes ≥98% of the perimeter 32 of the growth compartment 30. In any embodiment, the portion includes ≥99% of the perimeter 32 of the growth compartment 30. In any embodiment (e.g., during use after the device is inoculated, the portion includes 100% of the perimeter 32 of the growth compartment 30.

Base 10 is preferably a relatively stiff waterproof film made of a material (e.g., polyester, polypropylene, or polystyrene) that will not absorb or otherwise be adversely affected by water. Base 10 preferably is made using a material that is substantially nontransmissible to gaseous oxygen. Nonlimiting examples of suitable materials for base 10 include polyester films at least about 15 μm to at least about 180 μm thick, polypropylene films at least about 100 μm to at least about 200 μm thick and polystyrene films at least about 300 μm to about 380 μm thick. Other suitable bases include ethylene vinyl alcohol copolymer films, polyvinyl alcohol films, and polyvinylidene chloride films. Base 10 can be opaque, translucent, or, if observing colonies through the base 10 is desired, the base may be transparent.

The coversheet 20 is attached (e.g., adhesively attached) to the base 10 to define the growth compartment 30 and; optionally, if the coversheet is optically transmissive; to view the growth compartment during shipping, storage, incubation, and/or colony counting. Coversheet 20 is preferably a relatively stiff waterproof film made of a material (e.g., polyester, polypropylene, or polystyrene) that will not absorb or otherwise be adversely affected by water. Coversheets 20 are preferably transparent in order to facilitate the counting of colonies without opening the culture device 100, and are substantially impermeable to microorganisms and water vapor.

Generally, coversheets can be made of materials such as those used to make base 10. Coversheet 20 preferably is made using a material that is substantially nontransmissible to gaseous oxygen. Nonlimiting examples of suitable materials for base 10 include polyester films at least about 15 μm to at least about 180 μm thick, polypropylene films at least about 100 μm to at least about 200 μm thick and polystyrene films at least about 300 μm to about 380 μm thick. Other suitable bases include ethylene vinyl alcohol copolymer films, polyvinyl alcohol films, and polyvinylidene chloride films. As shown in FIG. 1, the coversheet 20 is bonded to the base 10 via the waterproof seal 40 that extends along a portion of the perimeter 32 of the growth compartment 30.

A person having ordinary skill in the art will recognize the transmissibility of oxygen gas through a given type of polymer film can be reduced by increasing the thickness of the polymer film. In any embodiment, the base and coversheet of the present disclosure are polymeric films having a suitable thickness to be substantially nontransmissible to gaseous oxygen.

The growth compartment 30 can be at any accessible location in the culture device 100 between the base 10 and the coversheet 20. Preferably, the perimeter 32 of the growth compartment 30, with the exception of the opening 34, is spaced apart from the peripheral edges 80 of the device 100.

A device of the present disclosure comprises a dry, cold-water-soluble gelling agent adhered to the base 10 in the growth compartment 30. Preferably, the gelling agent is adhered, either directly or indirectly, to the base 10. Optionally, the gelling agent is adhered directly or indirectly to the coversheet 20 of the device 100. In any embodiment, the gelling agent may be uniformly distributed onto the inner surface 10 of the base 10 and/or the inner surface of the coversheet 20 in the growth compartment 30 of the device 100.

In any embodiment, the gelling agent can be provided in the device as a first dry coating 14 adhered to the base 10. In any embodiment, the first dry coating 14 can be adhered to a first adhesive layer 12 adhered to the base 10 in the growth compartment 30. Suitable gelling agents for use in the first dry coating 14 include cold-water-soluble natural and synthetic gelling agents. Natural gelling agents such as algin, carboxymethyl cellulose, tara gum, hydroxyethyl cellulose, guar gum, locust bean gum, xanthan gum, and synthetic gelling agents such as polyacrylamide, polyurethane, polyethylene oxides, and mixtures thereof are generally suitable. Appropriate gelling agents can be selected according to the teaching of this disclosure and the disclosures of U.S. Pat. Nos. 4,565,783; 5,089,413; and 5,232,838. Other preferred gelling agents include hydroxypropyl methylcellulose; these gelling agents being useful individually, or preferably, in combination with another gelling agent such as one of the aforementioned gelling agents.

Thus, in any embodiment, a device 100 of the present disclosure optionally can comprise a first dry coating 14 adhered to at least a portion or all of the inner surface of the base 10 in the growth compartment 30. The first dry coating 14, if present, may comprise the dry, cold-water-soluble gelling agent. Optionally, a first adhesive layer 12 is adhered to the base 10 and at least a portion of the first dry coating is adhered to the first adhesive layer in the growth compartment 30.

The coversheet 20 can be free of any coating (not shown). Alternatively, if the device 100 does not have a first dry coating 14 adhered to the inner surface 10 of the base 10 in the growth compartment 30 or if the device 100 does have a first dry coating 14 adhered to the base 10, the coversheet 20 may comprise a second dry coating 24 adhered thereto in the growth compartment. The second dry coating 24, if present, may comprise the dry, cold-water-soluble gelling agent. Optionally, a second adhesive layer 22 is adhered to the coversheet 20 and at least a portion of the second dry coating 24 is adhered to the second adhesive layer in the growth compartment 30. In any embodiment, a portion of second adhesive layer 22 may be used to form the waterproof seal at the perimeter 32 of the growth compartment 30.

The first and/or second dry coating optionally can comprise any nutrient or nutrient culture medium that is cold-water-reconstitutable, that does not substantially interfere with the oxygen-scavenging reagent (discussed below) or the cold-water gelling properties of the gelling agent, and that facilitates growth of a sulfate-reducing microorganism. The particular nutrient or culture medium suitable for use in the culture device may depend on the microorganism to be grown in the device, and will be easily selected by those skilled in the art. A non-limiting example of a suitable nutrient culture medium comprises Bacto Tryptone, Amresco Soytone, Bacto Yeast Extract, $MgSO_4$-$7H_2O$, Sodium Lactate, Sodium Acetate, NaCl, $NH_4Cl$, with a pH of about 7.3, as described in Example 5 herein. Generally, such nutrients are cold-water soluble. Suitable nutrients for supporting bacterial growth are known in the art and include without limitation yeast extract, peptone, sugars, suitable salts, and the like. In any embodiment, the first and/or second dry coating further can comprise a selective agent (e.g., a nutrient, an antibiotic, and combinations thereof) that facilitates the growth of a sulfate-reducing microorganism or group of sulfate-reducing microorganisms over another microorganism or group of microorganisms that may otherwise grow in the culture device. Those skilled in the art will recognize that a variety of other formulations could be used and that these do not detract from the scope of this invention.

Preferably, when the first dry coating 14 consists primarily of dry powder or dry powder agglomerate, the first coating 14 is disposed on a first adhesive layer 12 that is disposed on at least a portion of the inner surface of the base 10. The first dry coating 14 can be deposited onto the base 10 or onto the optional first adhesive layer 12 using compounding processes, adhesive coating processes, and liquid-coating processes and/or dry-coating processes described, for example, in U.S. Pat. Nos. 4,565,783; 5,089,413; and 5,232,838; which are all incorporated herein by reference in their entirety.

Preferably, when the second dry coating 24 consists primarily of dry powder or dry powder agglomerate, the second coating 24 is disposed on a second adhesive layer 22 that is disposed on at least a portion of the inner surface of the coversheet 20. The second dry coating 24 can be deposited onto the coversheet 20 or onto the optional second adhesive layer 22 using compounding processes, adhesive coating processes, and liquid-coating processes and/or dry-coating processes described, for example, in U.S. Pat. Nos. 4,565,783; 5,089,413; and 5,232,838; which are all incorporated herein by reference in their entirety.

The growth compartment 30 is defined as a volume disposed between the inner surfaces of the base 10 and coversheet 20, the volume encompassing at least a portion of the first dry coating 14 and/or second dry coating 24. Thus, when an aqueous liquid is distributed into the growth compartment, the aqueous liquid is in fluidic contact with at least a portion of the first dry coating 14, if present, and/or second dry coating 24, if present. In any embodiment, the thickness of the growth compartment 30 of the uninoculated culture device may about 0.2 mm to about 3 mm. The thickness of the growth compartment 30 of an inoculated culture device of the present disclosure can vary depending upon, for example, the volume of aqueous liquid (not shown) deposited in the culture device and the presence of solids (e.g., suspended particulates and/or a membrane filter) associated with the sample (not shown). In any embodiment, the thickness of the growth compartment of the inoculated culture device can be about 1 mm to about 5 mm.

Culture devices of the present disclosure further comprise an effective amount of one or more dry oxygen-scavenging reagent. The one or more oxygen-scavenging reagent is disposed in the growth compartment; optionally, adhered to an adhesive layer in the growth compartment, as discussed herein. "Dry", as used herein, means the reagent is substantially water-free. The phrase "substantially water-free" refers to a reagent that has a water content no greater than about the water content of the material (e.g., provided as a powder or as a dehydrated aqueous coating) once it has been permitted to equilibrate with the ambient environment.

Optionally, a culture device of the present disclosure further can comprise other dry, water-rehydratable components such as a component of a buffer, a reducing agent, and/or an indicator reagent.

At least two dry components (e.g., the gelling agent and the one or more oxygen scavenging reagent or the reducing agent) is hydrated with an aqueous liquid before, during, or after the introduction (e.g., inoculation) of sample material into the growth compartment of the culture device, as described herein. Typically, the sample material and/or aqueous liquid is introduced into the growth compartment of the culture device in ambient conditions (i.e., in an aerobic gaseous environment). Thus, after inoculation of the growth compartment with a sample under aerobic conditions, the aqueous liquid in the growth compartment of the culture device comprises a first dissolved-oxygen concentration. The one or more oxygen-scavenging reagent in the culture device functions to reduce the first dissolved-oxygen concentration in the aqueous liquid in the growth compartment to a second dissolved-oxygen concentration that is substantially lower than the first dissolved-oxygen concentration. This reduction of the dissolved oxygen concentration in the growth compartment of the inoculated culture device facilitates the growth of obligately-anaerobic or microaerophilic microorganisms in the culture device.

In any embodiment, the effective amount of the one or more oxygen-scavenging reagent and concentration thereof is selected such that reducing the first dissolved oxygen concentration to the second dissolved oxygen concentration occurs within about 120 minutes after bringing the one or more oxygen-scavenging reagent into fluidic contact with the predefined volume of aqueous liquid in the growth compartment of the culture device. In any embodiment, the effective amount of the one or more oxygen-scavenging reagent and concentration thereof is selected such that reducing the first dissolved oxygen concentration to the second dissolved oxygen concentration occurs within about 60 minutes after bringing the oxygen-scavenging reagent into fluidic contact with the predefined volume of aqueous liquid in the growth compartment of the culture device. In any embodiment, the effective amount of the one or more oxygen-scavenging reagent and concentration thereof is selected such that reducing the first dissolved oxygen concentration to the second dissolved oxygen concentration occurs within about 30 minutes after bringing the oxygen-scavenging reagent into fluidic contact with the predefined volume of aqueous liquid in the growth compartment of the culture device.

In any embodiment, reducing the first dissolved oxygen concentration to the second dissolved oxygen concentration occurs at a temperature between ambient temperature (e.g., about 16 degrees C.) and about 80 degrees C., inclusive. Thus, in any embodiment of a method according to the present disclosure, it is not required to incubate the culture device at an elevated temperature (i.e., above ambient temperature) in order to reduce the first dissolved oxygen concentration to the second dissolved oxygen concentration after bringing the oxygen-scavenging reagent into fluidic contact with the predefined volume of aqueous liquid in the growth compartment of the culture device.

A person having ordinary skill in the art will recognize the amount of oxygen removed from the growth compartment of a culture device of the present disclosure within a period of time suitable for culturing microorganisms is dependent inter alia upon the quantity of the one or more oxygen-scavenging reagent in the growth compartment of the culture device. By adjusting the amount of oxygen-scavenging reagent in the growth compartment according to the present disclosure, the culture device can be configured for culturing microaerotolerant microorganisms or for culturing obligately anaerobic microorganisms.

A number of oxygen-scavenging reagents are known including, for example, ascorbic acid (e.g., L-ascorbic acid and salts thereof, an enzyme that catalyzes an oxygen-consuming reaction, ferrous iron salts, metal salts of sulfite, bisulfite, and metabisulfite. A suitable oxygen-scavenging reagent according to the present disclosure consumes enough oxygen to create a low-oxygen or anaerobic local environment in the culture device and produces quantities and types of reaction products that can be in fluidic communication with the microorganisms to be cultured in the device without substantially inhibiting growth of those microorganisms. In any embodiment, the oxygen-scavenging reagent is disposed in the growth compartment in a quantity of about 1 micromole/10 cm$^2$ to about 15 micromoles/10 cm$^2$.

Preferably, in any embodiment, the one or more oxygen-scavenging reagent is provided in the form of a dry powder. More preferably, in any embodiment, the one or more oxygen-scavenging reagent is provided as a dry powder that is milled and classified to form a population of particles with a size distribution consisting essentially of particles having a diameter of 100 microns or less. Advantageously, an oxygen-scavenging reagent provided in particles having a diameter of 100 microns or less can be adhered to the base or the coversheet (e.g., adhered to an adhesive layer coated onto the base or coversheet) in an amount effective to create and maintain (e.g., up to about 24 hours of incubation, up to about 48 hours of incubation, up to about 72 hours of incubation, up to 4 days of incubation, up to 5 days of incubation, up to 7 days of incubation, at least 24 hours of incubation, at least 48 hours of incubation, at least 72 hours of incubation, at least 4 days of incubation, at least 5 days of incubation, at least 7 days of incubation) an anaerobic environment in the growth compartment when the device is inoculated with a predefined volume of aqueous liquid and, optionally, the opening is sealed.

Adhesive used in the optional adhesive layer 22 disposed on the coversheet 20 can be the same as or different from the adhesive used in the optional adhesive layer 12 disposed on the base 10. In addition, the second dry coating 24 disposed on the coversheet 20 can be the same as or different from the first dry coating 14 disposed on the base 10. Coatings on coversheet 20 can cover the entire surface facing the base, but preferably cover at least a part of the inner surface that defines at least a portion of the growth compartment 30 of the culture device 100.

In any embodiment, a selective agent may be disposed in the device in a dry coating or, optionally, dissolved in an adhesive layer within the growth compartment.

Optionally, a culture device of the present disclosure further comprises a means for indicating oxygen in a culture device. Preferably, the means is capable of indicating a quantity (e.g., either a predetermined threshold quantity or a relative quantity) of oxygen present in the device. Advantageously, the means can indicate whether or when the oxygen-scavenging reagent has suitably depleted the oxygen in the growth compartment of the culture device to a concentration that facilitates the growth of microaerophilic, microaerotolerant or obligately-anaerobic microorganisms. Means for detecting oxygen in a culture device are known in the art and include, for example, redox dyes (e.g., methylene blue) and oxygen-quenched fluorescent dyes.

The means can be a luminescent compound that indicates the absence of oxygen inside of the device. Suitable oxygen indicators are disclosed in U.S. Pat. No. 6,689,438 (Kennedy et al.), which is incorporated herein by reference in its entirety. Luminescent compounds appropriate as indicators for a culture device of the present disclosure will display luminescence that is quenched by oxygen. More precisely, the indicators will luminesce upon exposure to their excitation frequency with an emission that is inversely proportional to the oxygen concentration. The indicator may be coated, laminated, or extruded onto another layer, or portion of another layer, within the device. Such a layer may be disposed in the growth compartment and optionally, is separated from the growth compartment by one or more other oxygen permeable layers. Suitable compounds for indicating oxygen include metallo derivatives of octaethylporphyrin, tetraphenylporphyrin, tetrabenzoporphyrin, the chlorins, or bacteriochlorins. Other suitable compounds include palladium coproporphyrin (PdCPP), platinum and palladium octaethylporphyrin (PtOEP, PdOEP), platinum and palladium tetraphenylporphyrin (PtTPP, PdTPP), camphorquinone (CQ), and xanthene type dyes such as erythrosin B (EB). Other suitable compounds include ruthenium, osmium and iridium complexes with ligands such as 2,2'-bipyridine, 1,10-phenanthroline, 4,7-diphenyl-1,10-phenanthroline and the like. Suitable examples of these include, tris(4,7-diphenyl-1,10-phenanthroline)ruthenium(II) perchlorate, tris(2,2'-bipyridine)ruthenium(II) perchlorate, tris (1,10-phenanthroline)ruthenium(II) perchlorate, and the like.

A culture device of the present disclosure optionally includes a dry buffer reagent disposed in the growth compartment that, when hydrated with deionized water, brings the water to a predefined pH that is suitable culture culturing and optionally selectively-enriching certain groups of microorganisms. For example, in any embodiment, the predefined pH may be about 5.2 to about 7.8. In any embodiment, the predefined pH may be less than or equal to 6.35 (e.g., about 4.5 to about 6.35).

Buffer reagents used in a device of the present disclosure include any microbiologically-compatible buffer having a $pK_a$ of about 8.0 or less. The acidic and basic parts of the buffer reagent are present in the culture device in a ratio such that, when a predefined volume of deionized water is contacted with the buffer reagent, the pH of the in the growth compartment is suitable for growth and detection of a particular microorganism or group of microorganisms. Suitable buffer reagents include, for example, a metal phosphate salt (e.g., sodium phosphate, potassium phosphate, calcium phosphate), a metal acetate salt (e.g., sodium acetate, potassium acetate, calcium acetate), 2-(N-morpholino)ethanesulfonic acid and sodium 2-(N-morpholino)ethanesulfonic acid, and succinic acid and sodium succinate. A person having ordinary skill in the art will recognize the ratio of acid an base buffer reagents can be adjusted in order to achieve the desired pH of the aqueous mixture formed when an predetermined volume of aqueous liquid (e.g., comprising the sample) is deposited in the growth compartment and the device is closed.

A culture device of the present disclosure optionally includes an indicator reagent. Suitable indicator reagents (e.g., triphenyltetrazolium chloride (TTC)) may detect substantially all microorganisms present in the culture device. Optionally, the indicator reagent may be a differential indicator; i.e., the indicator reagent distinguishes certain microorganisms from other microorganisms. Suitable indicator reagents include, for example, an indicator (e.g., ferrous ammonium sulfate, fluorescent $H_2S$ probes) to detect microbial hydrogen sulfide production, a pH indicator, a chromogenic enzyme substrate, and a fluorogenic enzyme substrate for detecting the presence of a microorganism. The indicator should not substantially interfere with the oxygen-scavenging reagent. In any embodiment, the indicator reagent may be disposed in the device in a dry coating or, optionally, dissolved in an adhesive layer within the growth compartment.

A culture device of the present disclosure optionally includes a reducing agent instead of, or in addition to, the dry oxygen-scavenging reagent. Suitable reducing reagents are useful to lower the oxidation-reduction potential of the growth medium and, thereby, facilitate growth of anaerobic microorganisms. Suitable reducing agents include, for example, sodium thioglycollate, L-cysteine, dithiothreitol, dithioerythritol, and combinations thereof.

In any embodiment, the growth compartment can be dimensioned to be hydrated with a 1 milliliter aqueous liquid volume. Water comprises about 0.54 µmoles of dissolved oxygen per milliliter. Thus, the first dry coating and/or second dry coating preferably comprises at least enough oxygen-scavenging reagent to consume 0.54 µmoles of oxygen in a period of 120 minutes or less at about 22 degrees C. to about 42 degrees C. More preferably, the first dry coating and/or second dry coating preferably comprises at least enough oxygen-scavenging reagent to consume more than 0.54 µmoles of oxygen in a period of 120 minutes or less at about 22 degrees C. to about 42 degrees C. In any embodiment, the growth compartment can be dimensioned to receive and be hydrated with about 2 to about 10 milliliters of aqueous liquid volume. A person having ordinary skill in the art will recognize the additional amount of oxygen-scavenging reagent needed to consume the oxygen in the aqueous sample in those situations.

In any embodiment, the first dry coating and/or second dry coating can include any number of other components, such as dyes (e.g., a pH indicator), crosslinking agents, reagents (e.g., selective reagents or indicator reagents such as chromogenic or fluorogenic enzyme substrates), or a combination of any two or more of the foregoing components. For example, for some uses it is desirable to incorporate an indicator of microbial growth (e.g., an indicator to detect hydrogen sulfide production, a pH indicator, a chromogenic enzyme substrate, a redox dye) in the first and/or second dry coating or in an adhesive layer of to which the first and/or second dry coating is adhered. Suitable dyes include those that are metabolized by or otherwise react with the growing microorganisms, and in so doing cause the colonies to be colored or fluorescent for easier visualization. Such dyes include triphenyl tetrazolium chloride, p-tolyl tetrazolium red, tetrazolium violet, veratryl tetrazolium blue and related dyes, and 5-bromo-4-chloroindolyl phosphate disodium salt. Other suitable dyes include those sensitive to pH changes during the growth of microorganisms, such as neutral red.

At least one dry coating can optionally include reagents necessary for carrying out certain microbiological tests. For example, antibiotics can be included for carrying out antibiotic susceptibility tests. For microorganism identification, differential reagents that undergo a color change in the presence of a particular type of microorganism can be included.

A culture device of the present can be prepared using a variety of techniques. Generally, a device can be made by hand or with common laboratory equipment as described herein and in U.S. Pat. Nos. 4,565,783; 5,089,413; and 5,232,838, for example.

A nonlimiting example of a suitable pressure-sensitive adhesive that can be used in the first adhesive layer and/or second adhesive layer is a copolymer of 2-methylbutylacrylate/acrylic acid in a mole ratio of 90/10. Other preferred pressure sensitive adhesives that can be used include isooctylacrylate/acrylic acid in a mole ratio of 95/5 or 94/6 and silicone rubber. Adhesives that turn milky (e.g., opaque) upon exposure to water are less preferred, but can be used in conjunction with a non-transparent base or in situations where colony visualization is not required. Heat-activated adhesives having a lower melting substance coated onto a higher melting substance and/or water-activated adhesives such as mucilage are also known and can be used in this invention. When incorporating an indicator reagent as described above in order to facilitate visualization of colonies, it is generally preferred to incorporate the indicator reagent in the adhesive or broth coating mixture, rather than in the powder.

The first adhesive layer or second adhesive layer is coated (e.g., using a knife coater) onto the top surface of base or coversheet to form an adhesive layer at a thickness that is preferably less than the average diameter of the particles of dry powder or agglomerated powder to be adhered to the adhesive. Generally, enough adhesive is coated in order to adhere the particles to the substrate (e.g., the first or coversheet described herein) but not so much that the particles become completely embedded in the adhesive. Generally, an adhesive layer about 5 µm to about 12 µm thick is suitable.

Preferably, when gelling agent is included in the first dry coating and/or second dry coating, it is included in an amount such that a predetermined quantity of water or an aqueous sample, e.g., 1 to 3 ml or more, placed in the growth compartment will form a hydrogel. For instance, 0.025 g to 0.050 g of powdered guar gum spread substantially uniformly over a surface area of 20.3 $cm^2$ will provide a sufficiently viscous medium when reconstituted with 1 to 3 ml of an aqueous sample. The size of the powder particles can be used to control the coating weight per unit area.

In any embodiment, the first dry coating or second dry coating can comprise one or more nutrients and/or a culture medium to facilitate growth of sulfate-reducing microorganisms. When the coating consists essentially of powders or powder agglomerates, the preferred ratio of gelling agent to nutrient in an adhered powder medium is determined by the particular microorganism to be grown on the device. For general purposes, however, a ratio from about 4 to 1 to about 5 to 1 (total gelling agent to total nutrient, based on weight) is preferred. The powder in an adhered powder medium can be applied to the adhesive layer (e.g., first adhesive layer 12 and/or second adhesive layer 22) by any means suitable for the application of a substantially uniform layer. Examples of suitable methods to apply the layer of powders include the use of a shaker-type device, or the use of a powder applicator.

A person having ordinary skill in the art will recognize suitable nutrients or culture media for use in a device of the present disclosure to grow and detect sulfate-reducing microorganisms. Non-limiting examples of suitable nutrients include a source of peptone (e.g., meat extract, meat peptone), yeast extract, an enzymatic digest of casein, and a carbohydrate (e.g., lactic acid). In any embodiment, the carbohydrate may be a nonfermentable nutrient that is utilizes by certain sulfate-reducing microorganisms. Preferably, the carbohydrate is present in the device in an amount that is high enough to facilitate growth (biomass production) of the microorganisms.

When using culture device of the present disclosure, an accurate count of the colonies of microorganisms present can be desirable. Thus, in any embodiment, a culture device of the present disclosure may comprise a grid pattern on base or, alternatively, on the coversheet. The grid pattern may comprise a square grid pattern such as, for example, the square grid pattern disclosed in U.S. Pat. No. 4,565,783. The grid pattern may be produced on the first or coversheet by any suitable process such as printing methods, for example.

In another aspect, the present disclosure provides a method of making the self-contained anaerobic environment-generating culture device of any of the above embodiments. The method comprises adhering a cold water-soluble gelling agent onto a portion of a base. The gelling agent may be dry (e.g., in the form of substantially water-free particles) when adhered to the base or the gelling agent may be adhered to the base as a liquid coating (e.g., an aqueous liquid coating) and subsequently dried to a substantially water-free state. The method further comprises attaching (e.g., via a pressure-sensitive adhesive) the base to a coversheet. Optionally, attaching the base to the coversheet further comprises forming the waterproof seal.

The base is positioned adjacent the cover sheet such that at least a portion of the adhered gelling agent faces the growth compartment disposed between the base and the coversheet. Optionally, in any embodiment, a first adhesive layer may be applied (e.g., using coating processes known in the art) to the base and the cold water-soluble gelling agent may be adhered to the first adhesive layer.

In an alternative embodiment, the cold water-soluble gelling agent may be adhered to the coversheet by any of the processes described for adhering the gelling agent to the base. Drying the adhered gelling agent, if the gelling agent is liquid-coated, can be performed by a number of processes known in the art. The coating can be dried in an oven (e.g., a gravity oven, a convection oven), for example, according to the process described in U.S. Pat. No. 5,601,998, which is incorporated herein by reference in its entirety. Preferably, the adhered gelling agent is dried until it is substantially water-free. As used herein, the phrases "substantially dry", "substantially water-free" or the like refer to a coating which has a water content no greater than about the water content of the dehydrated coating once it has been permitted to equilibrate with the ambient environment.

The method further comprises depositing one or more other dry components selected from the group consisting of the first and/or second oxygen-scavenging reagent, a buffer component, the culture medium, the reducing agent, the indicator reagent, and the selective agent. In any embodiment, any one or all of the oxygen-scavenging reagent and the component of the buffer system can be deposited into the growth compartment as a dry powder. Optionally, any one or all of oxygen-scavenging reagent and the buffer system may be adhered to an adhesive (e.g. a first adhesive layer or second adhesive layer as described herein) in the growth compartment. Other optional components (e.g., indicator reagents, selective agents, nutrients) may also be deposited into the growth compartment, optionally, adhered to an adhesive layer.

Figure 2A:
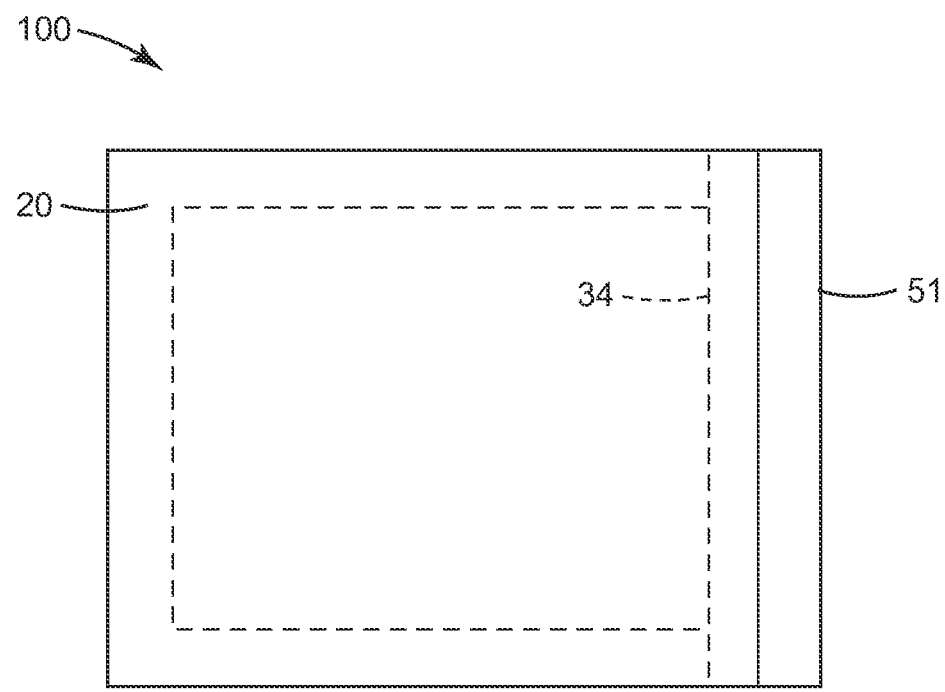
FIG. 2A is a plan view of an alternative embodiment of a culture device according to the present disclosure.
Figure 2B:
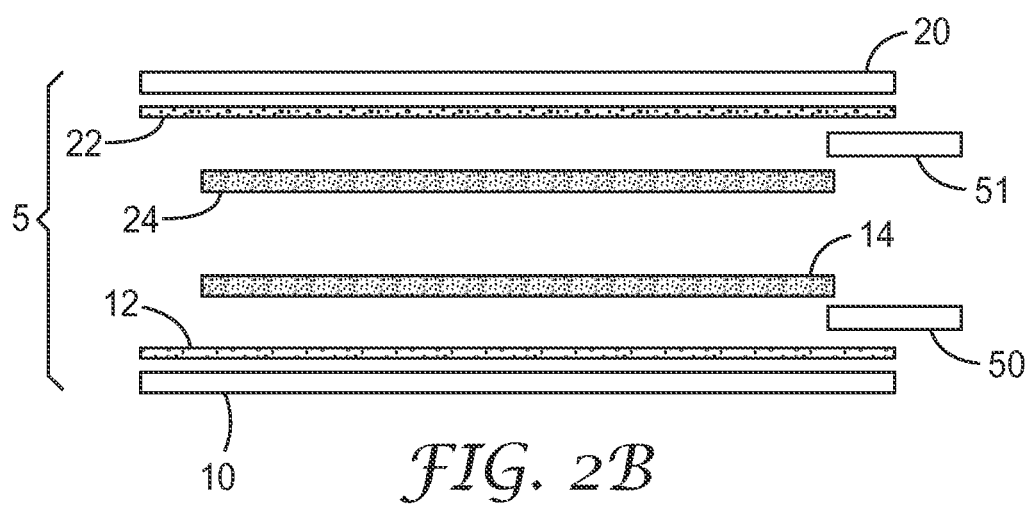
FIG. 2B is an exploded side view of the culture device of FIG. 2A.
Figure 3:
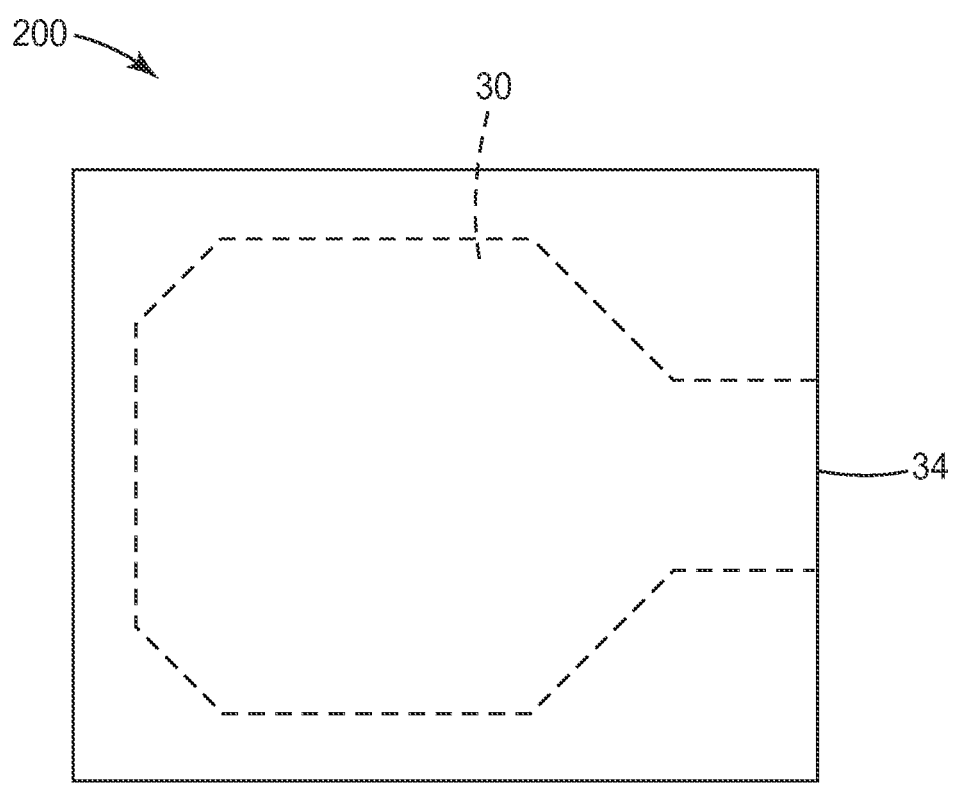
FIG. 3 is a plan view of yet another alternative embodiment of a culture device according to the present disclosure.

Positioning the base adjacent the coversheet, such that the adhered gelling agent faces the growth compartment disposed between the base and the coversheet can be performed in a variety of ways. A representative example of positioning the base and coversheets adjacent each other so that a portion of the gelling agent overlaps the growth compartment is shown in FIGS. 1-3. It can be seen that the overlapping configuration permits an operator to deposit an aqueous liquid between the base and the coversheet thereby placing the gelling agent, the oxygen-scavenging reagent, and other dry components present in the growth compartment into fluid communication.

In any embodiment, a culture device of the present disclosure may comprise optional removable tabs releasably adhered to an adhesive layer proximate the opening of the culture device. FIGS. 2A and 2B show one embodiment of a culture device 200 comprising a plurality of removable tabs (tabs 50 and 51, respectively) that are adhered to the first adhesive layer 12 and second adhesive layer 22, respectively, adjacent the opening 34 of the device. The removable tabs prevent the first and second adhesive layers from adhering to each other (and thereby sealing the opening) during storage and handling until after the device is inoculated and the tabs are removed by the operator.

Removable tabs 50 and 51 can be made from any suitable material (e.g., paper, polymer film) onto which a release coating (e.g., low-adhesion backsize) can be applied to prevent aggressive adhesion between the tab material and the adhesive layers.

The growth compartment of a device according to the present disclosure can have a variety of shapes such as, for example, the rectangular-shaped growth compartment of FIG. 1A. Other suitable shapes include, but are not limited to, circular, oval, polygonal, stellate, and irregular-shaped growth compartments. FIG. 3 shows one embodiment of a culture device 300 having a polygonal growth compartment with an opening 34 that defines less than about 10% of the perimeter of the growth compartment 30.

Figure 4A:
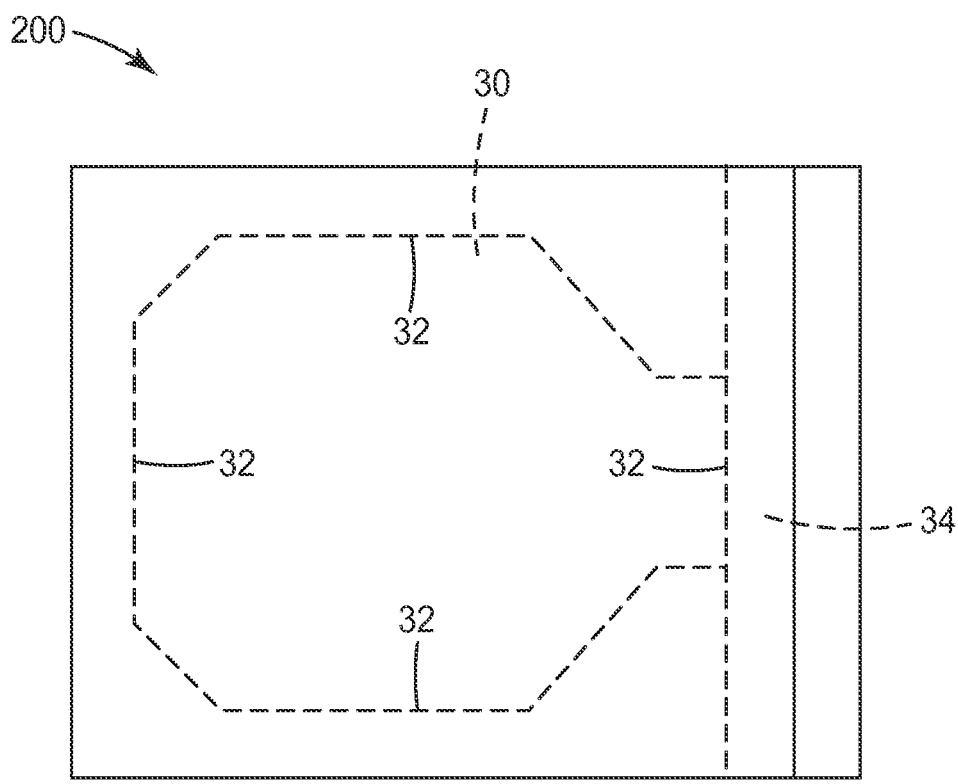
FIG. 4A is a plan view of an alternative embodiment of the culture device of FIG. 3.
Figure 4B:
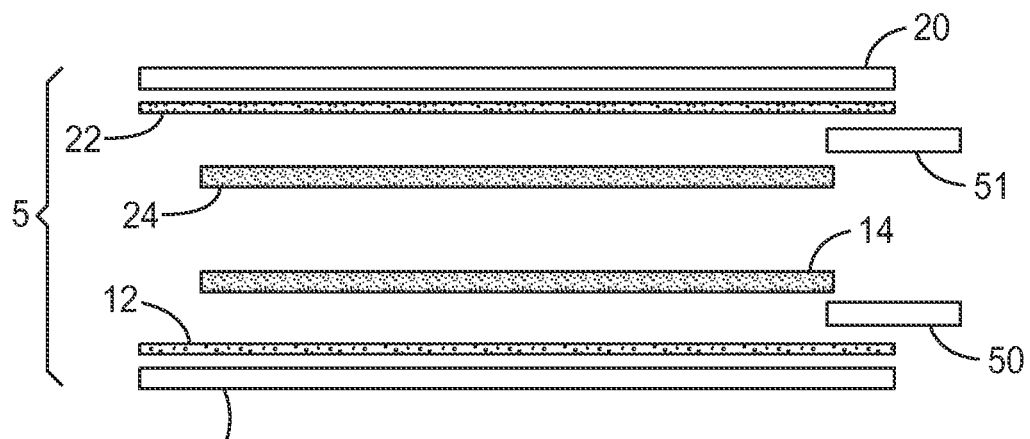
FIG. 4B is an exploded side view of the culture device of FIG. 4A.

FIGS. 4A and 4B show various views of the culture device 300 of FIG. 3, wherein the device 300 further comprises a plurality of removable tabs (tabs 50 and 51, respectively).

Figure 5A:
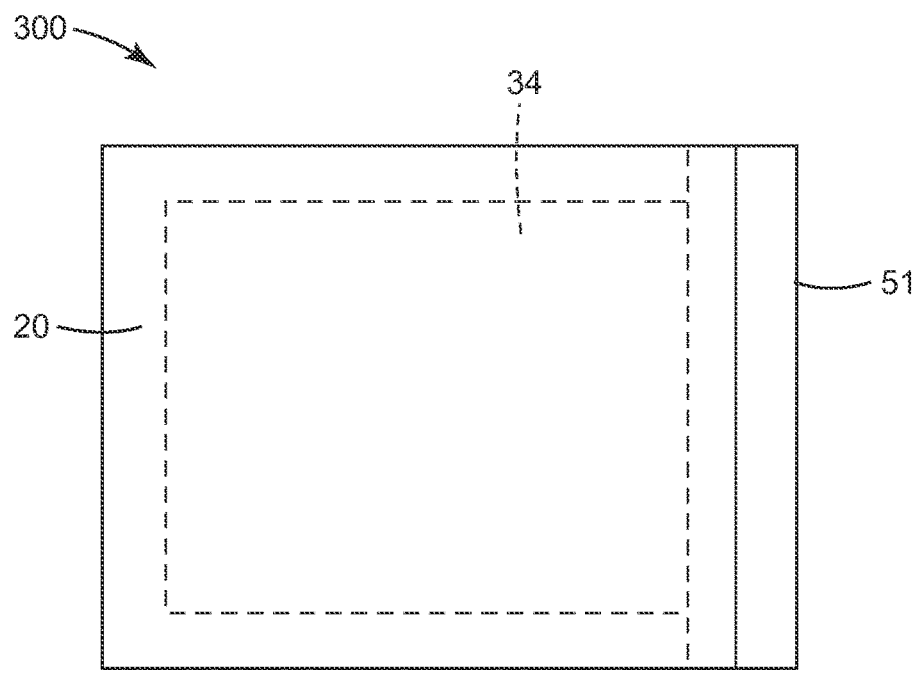
FIG. 5A is a plan view of yet another alternative embodiment of a culture device according the present disclosure.
Figure 5B:
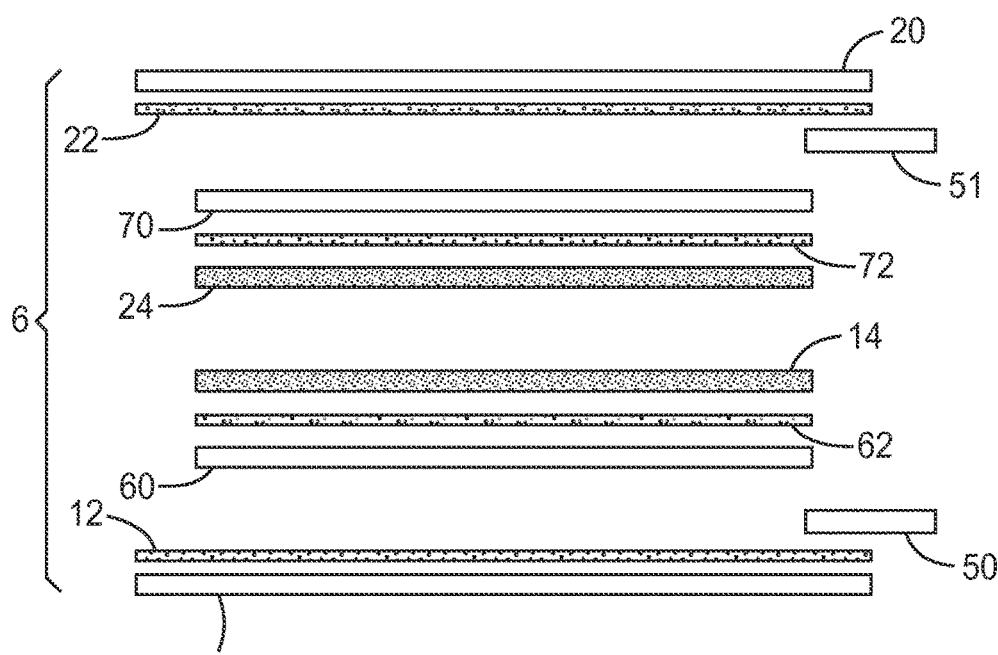
FIG. 5B is an exploded side view of the culture device of FIG. 5A.
Figure 6:
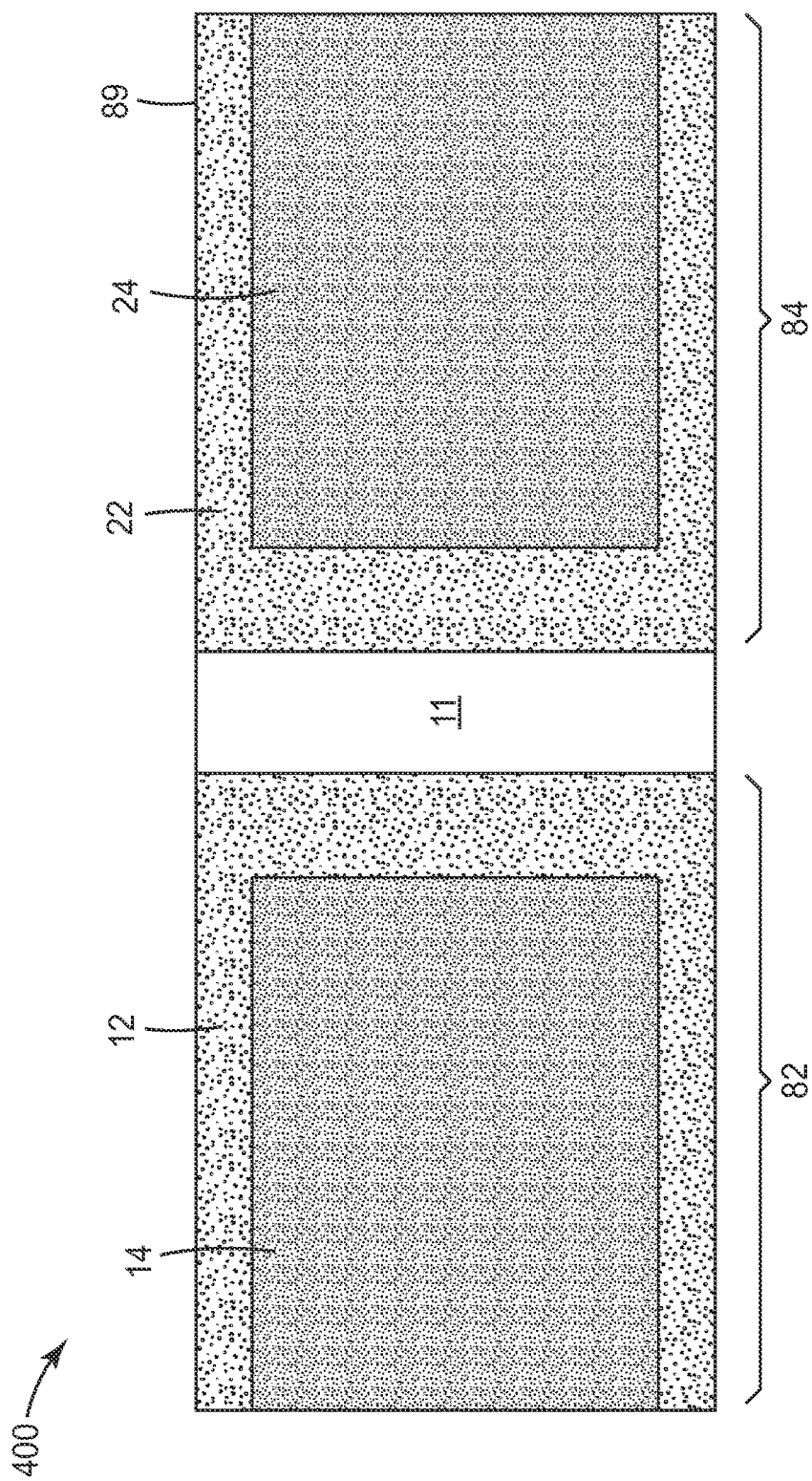
Figure 9:
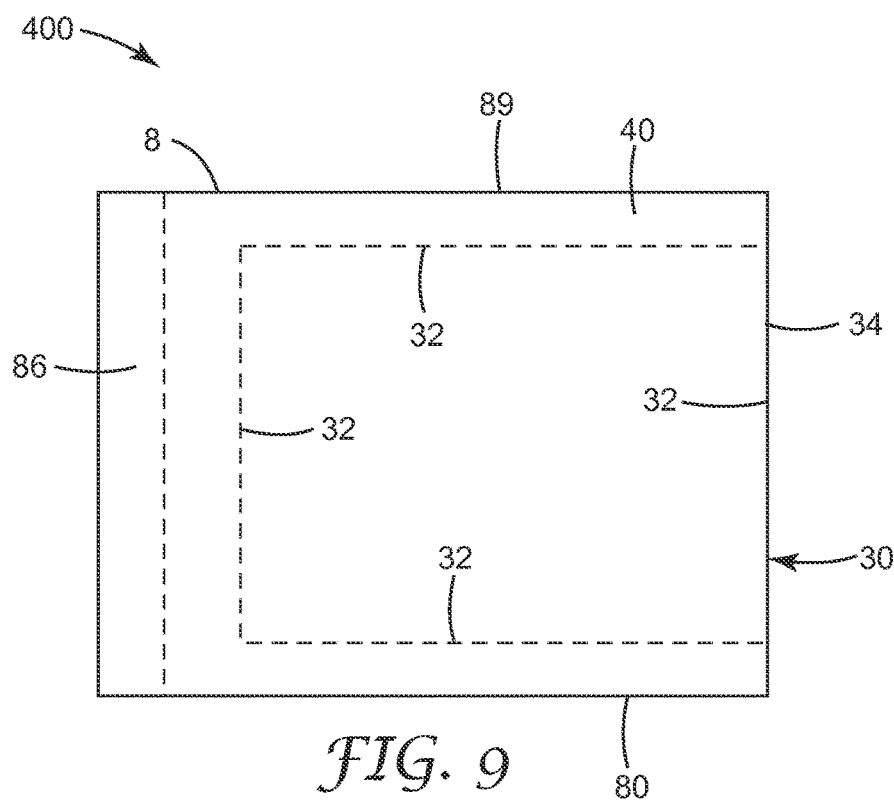

In any embodiment, a device according to the present disclosure can be fabricated by adhering at least one of the dry components (e.g., the gelling agent, the one or more oxygen-scavenging reagent, the reducing agent) to a carrier and, subsequently, adhering the carrier to the base or the coversheet in the growth compartment. FIGS. 5A and 5B show one embodiment of a culture device 300 comprising said carrier.

The device 300 comprises a body 6 having a base 10 and a coversheet 20 as described hereinabove. Adhered to the base 10 is the first adhesive layer 12 as described hereinabove. Adhered to the coversheet 20 is the second adhesive layer 22 as described hereinabove. Adhered to the first adhesive layer 12 is optional carrier 60. Adhered to the carrier 60 via an optional third adhesive layer 62 is the first dry coating 14 as described herein. Adhered to the second adhesive layer 22 is optional carrier 70. Adhered to the carrier 70 via an optional fourth adhesive layer 72 is the second dry coating 24 as described hereinabove. In any embodiment, a device according to the present disclosure can comprise the first carrier 60 (and dry coating thereon), the second carrier 70 (and dry coating thereon) or both the first and second carriers and dry coatings thereon.

The first and second carriers can be fabricated using any suitable material described herein for use as material for the base or the coversheet. The third adhesive layer and fourth adhesive layer can comprise any suitable adhesive described herein for use in the first or second adhesive layers.

It is now know that the inventive device 300 of FIGS. 5A and 5B can be readily coated and assembled using thin-film substrates for the base, the coversheet, and the carriers and using roll-to-roll processes.

It is now know that a device according to the present disclosure alternatively can be constructed using a unitary substrate to form both the coversheet and the base. In these embodiments, the coatings are applied to a unitary, substantially flat substrate, which is subsequently folded in order to create the waterproof seal and the growth compartment disposed between two portions of the unitary substrate.

FIGS. 6-9 show one embodiment of a device 400 of the present disclosure wherein the device is constructed from a unitary substrate. The device 400 comprises a body 8 that includes a waterproof substrate 11. The waterproof substrate has a first major surface 81 and a second major surface 87 opposite the first major surface. The first major surface 81 comprises a first section 82 and a second section 84 spaced apart from the first section. The body 8 further comprises an edge 89 and a fold 86 that places a first section 82 in overlapping juxtaposition with respect to the second section 84.

The first section 82 and the second section 84 define inner walls of a growth compartment 30 that comprises a perimeter 32 and an opening 34 that provides liquid access to the growth compartment. A portion of the perimeter 32 is defined by a waterproof seal 40, wherein the portion includes >50% of the perimeter. In any embodiment, the portion includes >50% of the perimeter 32 of the growth compartment 30. In any embodiment, the portion includes ≥80% of the perimeter 32 of the growth compartment 30. In any embodiment, the portion includes ≥90% of the perimeter 32 of the growth compartment 30. In any embodiment, the portion includes ≥95% of the perimeter 32 of the growth compartment 30. In any embodiment, the portion includes ≥98% of the perimeter 32 of the growth compartment 30. In any embodiment, the portion includes ≥99% of the perimeter 32 of the growth compartment 30. In any embodiment (e.g., during use after the device is inoculated, the portion includes 100% of the perimeter 32 of the growth compartment 30.

A dry cold water-soluble gelling agent is adhered to at least one of the sections (e.g., the first section or the second section 84) of the growth compartment 30. The gelling agent may be provided as a part of a first coating 14, which optionally may be adhered to a first adhesive layer 12 that is adhered to the first section 82. Alternatively, or additionally, the gelling agent may be provided as a part of a second coating 24, which optionally may be adhered to a second adhesive layer 22 that is adhered to the second section 84. In any embodiment, the first and second adhesive layers and first and second coatings are as described hereinabove.

In any embodiment, a dry oxygen-scavenging reagent and/or an indicator reagent (e.g., a dry indicator reagent) for detecting hydrogen sulfide production by a sulfate-reducing bacterium is disposed in the growth compartment 30. In any embodiment, the oxygen-scavenging reagent and/or the indicator reagent for detecting hydrogen sulfide production by a sulfate-reducing bacterium may be disposed in the growth compartment 30 as a loose powder or it may be part of the first dry coating 14 adhered to the first section 82 and/or a part of the second dry coating 24 adhered to the second section 84.

In any embodiment, the device 400 further can comprise a dry reducing agent, an indicator reagent, a nutrient or culture medium, and/or a buffer reagent, as discussed hereinabove.

In any embodiment, the first dry coating 14 and/or second dry coating 24 of the device 400 may be adhered to a carrier (not shown) as described hereinabove.

Figure 10:
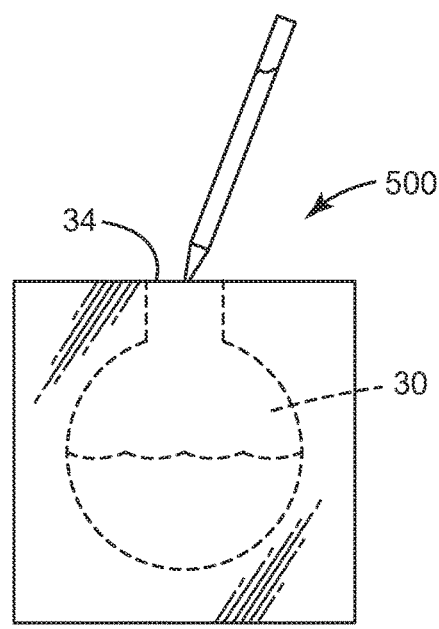
FIG. 10 is a schematic plan view of one embodiment of a process for inoculating a culture device of the present disclosure.

After the device is assembled, it can be inoculated with a sample. FIG. 10 shows one embodiment of an inoculated culture device 500. The device 500 is positioned with the opening 34 above the growth compartment 30. A liquid sample is transferred through the opening 34 via a pipet, for example. Optionally, after the sample is transferred to the growth compartment, the opening 34 is sealed as described herein and the device 500 is incubated at a temperature that facilitates growth of a sulfate-reducing microorganism.

FIGS. 11A-11E illustrate one embodiment of a method of making a device according to the present disclosure. In any embodiment, a substantially planar waterproof base 10 has a first layer of pressure-sensitive adhesive 12 coated on a major surface. Suitable bases and adhesives are described hereinabove. Prior to applying a coating over the first adhesive layer 12, a sheet-like mask 95 is applied (e.g., laminated) to the first adhesive layer 12 on the base 10. The mask 95 has a peripheral edge, a central open area, and a gap extending from the open area to the perimeter 32. When placed on the base 10, the opening and gap of the mask 95 expose a portion of the first adhesive layer 12. Although shown as having a circular shape, it is contemplated that the open area may have any of a number of suitable shapes (e.g., circular, square, oval, oblong, rectangular, polygonal, or the like).

The mask 95 can be fabricated from a variety of materials including, for example, sheets of paper or plastic film. Preferably, the mask 95 is coated with a low-adhesion backsize on the side that is placed against the first adhesive layer 12. The low-adhesion backsize (not shown) facilitates removal of the mask from the adhesive without disrupting the bond between the adhesive and the base. After the mask 95 is applied to the first adhesive layer 12, a first dry coating 14 (e.g., a coating of a powder material such as the gelling agent, the oxygen-scavenging agent, and/or other dry components as described hereinabove) is applied to the exposed adhesive. FIG. 4c shows the first dry coating 14 adheres to the portions of the adhesive that are not covered by the mask 95.

Figure 11A:
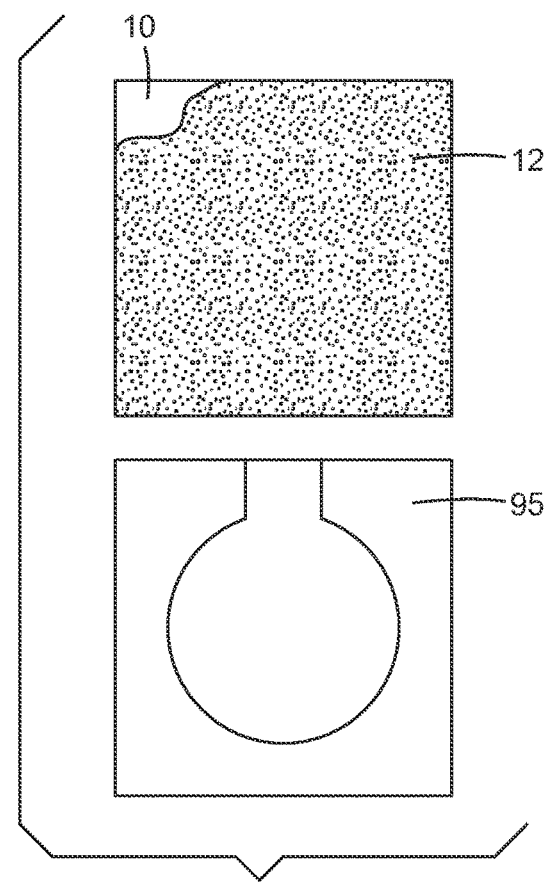
FIGS. 11A-11E are schematic plan views of various steps of one embodiment of a process for making a culture device according to the present disclosure.
Figure 11B:
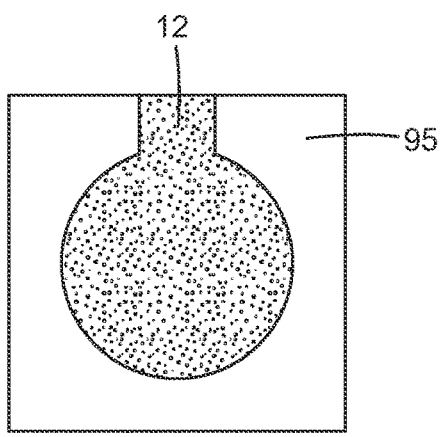
Figure 11C:
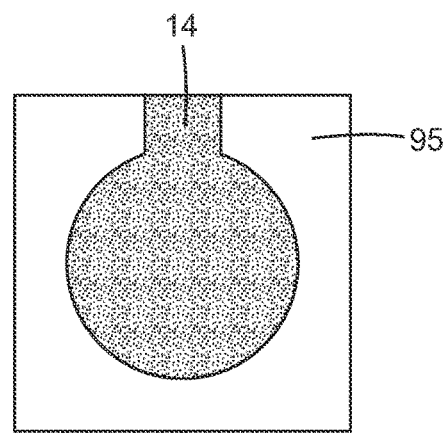
Figure 11D:
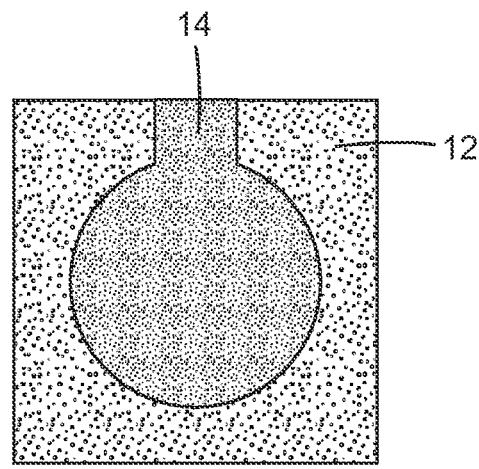
Figure 11E:
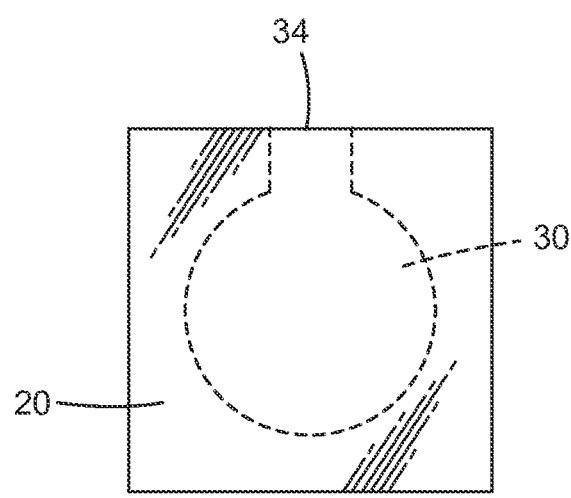

After applying the first dry coating 14, excess powder optionally can be removed (e.g., by vibration) and the mask 95 is removed. Removing the mask 95 exposes the remaining uncoated first adhesive layer 12 on the base 10, as shown in FIG. 11D. To complete the preparation of a device according to the present disclosure, a coversheet 20 dimensioned to cover the exposed first adhesive layer 12 is laminated (e.g., using a roller, not shown) to the adhesive, as shown in FIG. 11E. The device comprises a growth compartment 30 into which a liquid sample (not shown) is introduced through the opening 34 along an edge of the device.

In yet another aspect, the present disclosure provides a method of detecting a sulfate-reducing microorganism. The method uses any embodiment of the culture devices described herein.

In any embodiment, the method comprises depositing a sample and a predefined volume of aqueous liquid into the growth compartment via the opening, optionally sealing the opening, incubating the culture device for a period of time sufficient to permit formation of a microbial colony in the growth compartment, and detecting the microbial colony. Optionally, the sample may comprise or may be suspended in the predefined volume of aqueous liquid. In any embodiment, depositing the sample with the predefined volume of aqueous liquid into the growth compartment comprises forming a semi-solid microbial culture medium enclosed (e.g., isolated from the external gaseous environment) in the growth compartment of the culture device.

In any embodiment, the predetermined volume of aqueous liquid used to hydrate and/or inoculate the culture device is about 0.1 milliliter to about 100 milliliters. In any embodiment, the predetermined volume of aqueous liquid used to hydrate and/or inoculate the culture device is about 1 milliliter to about 20 milliliters. In any embodiment, the predetermined volume of aqueous liquid used to hydrate and/or inoculate the culture device is about 1 milliliter. In any embodiment, the predetermined volume of aqueous liquid used to hydrate and/or inoculate the culture device is about 2 milliliters. In any embodiment, the predetermined volume of aqueous liquid used to hydrate and/or inoculate the culture device is about 3 milliliters. In any embodiment, the predetermined volume of aqueous liquid used to hydrate and/or inoculate the culture device is about 4 milliliters. In any embodiment, the predetermined volume of aqueous liquid used to hydrate and/or inoculate the culture device is about 5 milliliters. In any embodiment, the predetermined volume of aqueous liquid used to hydrate and/or inoculate the culture device is about 10 milliliters. In any embodiment, the aqueous liquid used to hydrate the growth region of the culture device is distributed over an area that results in about one milliliter per 3.9 $cm^2$ of growth region to about one milliliter of liquid per 20.3 $cm^2$ of growth region.

In any embodiment of the method, placing the predetermined volume into the growth compartment comprises simultaneously placing the sample into the growth compartment. For example, the sample may be a liquid (e.g., a water or beverage sample to be tested for microbial contamination) or the sample may be a solid or semisolid sample suspended in a liquid carrier or diluent.

Alternatively, in any embodiment, placing the predetermined volume into the growth compartment does not comprise simultaneously placing the sample into the growth compartment. For example, the sample may comprise a liquid, a solid, or a semisolid material that is placed into the growth compartment before or after a predefined volume of (preferably sterile) liquid carrier or diluent is placed into the growth compartment of the culture device.

Advantageously, the culture device can be hydrated and/or inoculated in an aerobic environment (i.e., in air). Typically, an aqueous liquid (which may include sample material to be tested) used to hydrate the device is pipetted onto the growth compartment between the base and the coversheet. After the predefined volume of aqueous liquid is deposited into the growth compartment, the culture device is optionally sealed (e.g., by removing one or more removable tabs, if present, to expose an adhesive layer that ca be used to seal the opening. Optionally, a flat or concave spreader, similar to those used to inoculate PETRIFILM culture devices, can be used to distribute the aqueous liquid evenly throughout the growth compartment.

In any embodiment of the method, placing the predetermined volume into the growth compartment can comprise simultaneously placing the sample into the growth compartment. In these embodiments, the sample may comprise an aqueous liquid and/or the sample may be diluted into or suspended in an aqueous liquid (e.g., a buffer or a sterile culture medium).

Alternatively, in any embodiment, placing the predetermined volume into the growth compartment does not comprise simultaneously placing the sample into the growth compartment. In these embodiments, a predetermined volume of aqueous liquid can be placed (e.g., pipetted, as shown in FIG. 10) into the growth compartment before or after placing the sample into the growth compartment. For example, the sample may be captured onto a membrane filter (no shown), which is placed into the growth compartment before or after the gelling agent is hydrated with aqueous liquid.

In any embodiment of the method, placing the sample into the growth compartment comprises placing one or more additive into the growth compartment. The one or more additive can be placed into the growth compartment with the sample or separately. The one or more additive may perform a variety of functions in the method. For example, in any embodiment, the one or more additive may comprise a nutrient and/or a culture medium to facilitate growth of sulfate-reducing microorganisms in the device. Such nutrients and culture media are well known in the art and may be selected based upon the particular microorganism to be cultured. The nutrient and culture medium should not substantially interfere with the oxygen-scavenging reagent. This can be tested readily by using an oxygen sensor as described in Examples 2-3 of International Publication No. WO2015/061213, which is incorporated herein by reference in its entirety.

Alternatively or additionally, in any embodiment, the additive comprises one or more selective agent (e.g., an antibiotic, a salt) that favors growth of one sulfate-reducing microorganism over at least one other microorganism (e.g., a non-sulfate-reducing microorganism). Alternatively or additionally, in any embodiment, the additive comprises an indicator reagent (e.g., indicator reagent for detecting hydrogen sulfide production by a sulfate-reducing bacterium, a pH indicator, a redox indicator, a chromogenic enzyme substrate, a fluorogenic enzyme substrate) for detecting the presence of a sulfate-reducing microorganism. A person having ordinary skill in the art will recognize selective agents and indicator reagents useful for detecting sulfate-reducing microorganisms. The selective agent and/or indicator should not substantially interfere with the oxygen-scavenging reagent. This can be tested readily by using an oxygen sensor as described above.

When contacted by aqueous liquid in the growth compartment; the dry components (e.g., the oxygen-scavenging reagent, a buffer reagent, the nutrient, the indicator reagent, the reducing agent, and/or the selective agent) and the aqueous liquid form a mixture that comprises a first concentration of dissolved oxygen.

In any embodiment, the first concentration of dissolved oxygen in the aqueous mixture in the growth compartment may be a concentration that substantially inhibits growth of an obligately-anaerobic microorganism, a microaerophilic microorganism, and/or a microaerotolerant microorganism. In these embodiments, placing the components in aqueous fluid communication initiates an oxygen-scavenging reaction, thereby reducing the first concentration of dissolved oxygen in the aqueous liquid in the growth compartment to a second concentration that is lower than the first concentration (e.g., at least about 50% lower, at least about 60% lower, at least about 70% lower, at least about 80%, at least about 90%, at least about 95%, at least about 98%, at least about 99% lower, or greater than 99% lower than the first concentration).

In any embodiment, reducing the first concentration of dissolved oxygen to the second concentration of dissolved oxygen can comprise reducing the dissolved oxygen in the aqueous mixture in the growth compartment to a second concentration that is low enough to support the growth of anaerobic microorganisms (e.g., aerotolerant bacteria or obligately anaerobic bacteria).

In any embodiment, reducing the first concentration of dissolved oxygen to the second concentration of dissolved oxygen comprises reducing the dissolved oxygen to the second concentration in the aqueous mixture in the growth compartment in less than or equal to about 120 minutes after the mixture is formed. In any embodiment, reducing the first concentration of dissolved oxygen to the second concentration of dissolved oxygen comprises reducing the dissolved oxygen to the second concentration in the aqueous mixture in the growth compartment in less than or equal to about 90 minutes after the mixture is formed. In any embodiment, reducing the first concentration of dissolved oxygen to the second concentration of dissolved oxygen comprises reducing the dissolved oxygen to the second concentration in the aqueous mixture in the growth compartment in less than or equal to about 60 minutes after the mixture is formed. In any embodiment, reducing the first concentration of dissolved oxygen to the second concentration of dissolved oxygen comprises reducing the dissolved oxygen to the second concentration in the aqueous mixture in the growth compartment in less than or equal to about 45 minutes after the mixture is formed. In any embodiment, reducing the first concentration of dissolved oxygen to the second concentration of dissolved oxygen comprises reducing the dissolved oxygen to the second concentration in the aqueous mixture in the growth compartment in less than or equal to about 30 minutes after the mixture is formed.

If the culture device is hydrated before sample material is placed into the device, the cold-water-soluble gelling agent optionally may be permitted to hydrate and form gel (e.g., at room temperature) for several minutes up to about 30 minutes or more before the device is reopened to inoculate with the culture material. During the period in which the gelling agent is permitted to hydrate and form a gel, the oxygen-scavenging reagent reduces the concentration of dissolved oxygen in the hydrated gelling agent from a first concentration to a second concentration that facilitates growth of anaerobic, sulfate-reducing microorganisms, as discussed herein.

Before or after the growth compartment of the culture device is hydrated, sample material can be contacted with the growth compartment in a variety of ways that are known in the art. In any embodiment, the sample material is contacted with the growth compartment by depositing the sample material into the growth compartment. This can be done, for example, by pipetting, by contacting the growth compartment with a swab (e.g. via the opening) that was used to obtain the sample material (e.g., by swabbing a surface), by contacting the growth compartment with an inoculating loop or needle (e.g., using a streak-plate technique), or by placing a sample capture device (e.g., a swab, sponge, or membrane filter) directly into the growth compartment. After the sample is deposited and the culture device is optionally sealed (taking care not to entrap macroscopically-visible air bubbles in the culture device), the oxygen-scavenging reagent depletes the dissolved oxygen in the growth compartment.

In any embodiment of the method, after the sample is placed into the growth compartment and optionally sealed, the culture device is incubated for a period of time (e.g., a predetermined period of time). The incubation conditions (e.g., the incubation temperature) can affect the rate of growth of the microorganisms, as is well known by a person having ordinary skill in the art. For example, incubation at lower temperatures (e.g., below about 25° C.) can allow for the detection of psychrotrophic microorganisms. Incubation at higher temperatures (e.g., about 30° C., about 32° C., about 35° C., about 37° C.) may facilitate faster growth of certain mesophilic microorganisms.

In some embodiments, after inoculation, the culture device can be incubated for at least about 16 hours, at least about 18 hours, at least about 24 hours, or at least about 48 hours. In some embodiments, the culture device can be incubated not more than about 24 hours, not more than about 48 hours, or not more than about 72 hours. In certain preferred embodiments, the culture device is incubated about 24 hours to about 48 hours. In any embodiment, the culture device can be incubated, and maintain a reduced-oxygen environment therein, for about 72 hours, for about 96 hours, for about 120 hours, for about 7 days, or for about 8 days before detecting or counting microbial colonies growing in the growth compartment. In any embodiment, incubating the culture device for a period of time sufficient to permit formation of a microbial colony comprises incubating the culture device for the period of time in an aerobic atmosphere (i.e., the culture device is not placed into a reduced-oxygen container or glovebox for incubation).

After the inoculated culture device is incubated, the method further comprises detecting a microbial colony. Microbial colonies can be detected in the culture device by a variety of techniques that are known in the art. After a suitable incubation period, the absence of a microorganism can be detected in a culture device by the absence of observable colonies, the absence of a change in a growth indicator (e.g., a pH indicator, a chromogenic enzyme substrate, a redox indicator such as TTC, a fluorogenic enzyme substrate) and the absence of gas bubbles associated with the metabolism of the fermentable carbohydrate in the growth medium.

An acid zone associated with a colony of microorganisms can be detected visually and/or by the use of an imaging system. For example, in a method wherein the culture medium comprises bromcresol purple as a pH indicator, the culture medium will have a purple or gray appearance at about a neutral pH. As the microorganisms grow and ferment a carbohydrate (e.g., glucose) in the culture medium, the bromcresol purple indicator will appear yellow adjacent the growing bacterial colonies. For example, in a method wherein the culture medium comprises chlorophenol red as a pH indicator, the culture medium will have a red or violet appearance at about a neutral pH. As the microorganisms and ferment a carbohydrate in the culture medium, the chlorophenol red indicator will appear yellow adjacent the growing microbial colonies.

Gas bubbles, if present in the growth compartment and associated with a colony of microorganisms (e.g., either touching the colony or within a distance of about 1 mm or less from the colony), can be detected visually and/or by the use of an imaging system. The gas bubbles may be associated with a visible colony and/or an acid zone detectable by a change in the color of a pH indicator in a region adjacent the colony of microorganisms. The gas bubble may comprise carbon dioxide generated by anaerobic fermentation of a carbohydrate, for example.

In any of the above embodiments, the method further can comprise obtaining an image of the culture device. In these embodiments, detecting the presence or absence of a colony of sulfate-reducing microorganisms comprises displaying, printing, or analyzing the image of the culture device. The imaging system comprises an imaging device and may comprise a processor. In some embodiments, the imaging device can comprise a line-scanner or an area scanner (e.g., a camera). The imaging device can include a monochromatic (e.g., black-and-white) or a polychromatic (e.g., color) scanner. Advantageously, monochromatic imaging systems can provide higher resolution images, which may improve the accuracy of the result and/or reduce the time necessary to detect the presence of microorganisms in the culture device.

In some embodiments, the imaging system further comprises an illumination system. The illumination system may include at least one source of broad-spectrum visible light (e.g., a "white" light). In some embodiments, the illumination system may include at least one source of narrow-spectrum visible light (e.g., a light-emitting diode that emits a relatively narrow bandwidth of visible light such as, for example, red, green, or blue light). In certain embodiments, the illumination system may include a source of narrow-spectrum visible light (e.g., a light-emitting diode) with a light emission peak at a preselected wavelength (e.g., about 525 nm).

The image can be obtained from light reflected by the components (e.g., microbial colonies, growth media, and indicators) in the growth compartment of the culture device or the image can be obtained from light transmitted through the components in the growth compartment of the culture device. Suitable imaging systems and corresponding illumination systems are described, for example, in International Patent Publication No. WO 2005/024047 and U.S. Patent Application Publication Nos. US 2004/0101954 and US 2004/0102903, each of which is incorporated herein by reference in its entirety. Non-limiting examples of suitable imaging systems include PETRIFILM Plate Reader (PPR), available from 3M Company (St. Paul, Minn.), the PETRISCAN Colony Counter available from Spiral Biotech (Norwood, Mass.), and PROTOCOL and ACOLYTE plate scanners available from Synbiosis (Cambridge, U.K.).

In some embodiments, obtaining an image comprises obtaining a wavelength-biased image. For example, the imaging system can include a bias filter that biases the light collected by the imaging device. Filter elements are known in the art and include both "cut-off" filters (i.e., filters that allow the passage of light wavelengths either above or below a certain specified wavelength) and "band-pass" filters (i.e., filters that allow the passage of light wavelengths between certain specified upper and lower limits). A bias filter can be positioned between the illumination source and the culture device. Alternatively or additionally, a bias filter can be positioned between the culture device and the imaging device.

EXEMPLARY EMBODIMENTS

Embodiment A is a device, comprising:
a body comprising a waterproof base, a waterproof coversheet attached to the base, and a growth compartment disposed therebetween, the growth compartment having a perimeter and an opening that provides liquid access to the growth compartment;
  wherein a portion of the perimeter is defined by a waterproof seal, wherein the portion includes >50% of the perimeter;
  a dry cold water-soluble gelling agent adhered to the base in the growth compartment;
  a dry culture medium disposed in the growth compartment, the culture medium selected to facilitate growth of a sulfate-reducing bacterium; and
  a dry first oxygen-scavenging reagent disposed in the growth compartment.

Embodiment B is the device of Embodiment A, wherein the device comprises an indicator reagent for detecting hydrogen sulfide production by a sulfate-reducing bacterium, wherein the indicator reagent is disposed in the growth compartment.

Embodiment C is a device, comprising:
a body comprising a waterproof base, a waterproof coversheet attached to the base, and a growth compartment disposed therebetween, the growth compartment having a perimeter and an opening that provides liquid access to the growth compartment;
  wherein a portion of the perimeter is defined by a waterproof seal, wherein the portion includes >50% of the perimeter;
  a dry cold water-soluble gelling agent adhered to the base in the growth compartment;
  an indicator reagent for detecting hydrogen sulfide production by a sulfate-reducing bacterium, wherein the indicator reagent is disposed in the growth compartment; and
  a dry first oxygen-scavenging reagent disposed in the growth compartment.

Embodiment D is the culture device of Embodiment C, further comprising a dry culture medium disposed in the growth compartment, the culture medium selected to facilitate growth of a sulfate-reducing bacterium.

Embodiment E is the device of any one of the preceding Embodiments, wherein the body is substantially two-dimensional.

Embodiment F is the device of any one of the preceding Embodiments, further comprising an effective amount of a dry reducing agent disposed in the growth compartment.

Embodiment G is the device of Embodiment F, wherein the reducing agent is adhered to the base.

Embodiment H is the device of any one of the preceding Embodiments, wherein the first oxygen-scavenging reagent is adhered to the base.

Embodiment I is the device of any one of the preceding Embodiments, wherein the culture medium comprises an organic carbon source.

Embodiment J is the device of Embodiment I, wherein the organic carbon source is nonfermentable.

Embodiment K is the device of any one of the preceding Embodiments, further comprising an indicator reagent for detecting a presence of a viable microorganism, wherein the indicator reagent is disposed in the growth compartment.

Embodiment L is the device of any one of the preceding Embodiments, further comprising a dry second oxygen-scavenging reagent disposed in the growth compartment.

Embodiment M is the device of Embodiment L, wherein the second oxygen-scavenging reagent is adhered to the waterproof base.

Embodiment N is the device of any one of the preceding Embodiments, wherein the indicator reagent is the first oxygen-scavenging reagent or the second oxygen-scavenging reagent.

Embodiment O is the device of any one of the preceding Embodiments, wherein a first dry component selected from the group consisting of the first oxygen-scavenging reagent, the second oxygen-scavenging reagent, the reducing reagent, the nutrient, the indicator reagent and a combination of any two or more of the foregoing components is adhered to the base.

Embodiment P is the device of Embodiment O, wherein the base comprises a first adhesive layer disposed thereon in at least a portion of the growth compartment, wherein the first dry component is adhered to the first adhesive layer in the growth compartment.

Embodiment Q is the device of Embodiment O, further comprising a first carrier, wherein the first dry component is adhered to the first carrier, wherein the first carrier is adhered to the first adhesive layer in the growth compartment.

Embodiment R is the device of Embodiment Q, wherein the first carrier comprises a second adhesive layer coated thereon, wherein the first dry component is adhered to the second adhesive layer.

Embodiment S is the device of any one of the preceding Embodiments, wherein a second dry component selected from the group consisting of the first oxygen-scavenging reagent, the second oxygen-scavenging reagent, the reducing reagent, the nutrient, the indicator reagent and a combination of any two or more of the foregoing components is adhered to the coversheet.

Embodiment T is the device of Embodiment S:
wherein the coversheet comprises a third adhesive layer disposed thereon in at least a portion of the growth compartment;
wherein the second dry component is adhered to the third adhesive layer in the growth compartment.

Embodiment U is the device of Embodiment T, further comprising a second carrier, wherein the second dry component is adhered to a second carrier, wherein the second carrier is adhered to the second adhesive layer in the growth compartment.

Embodiment V is the device of Embodiment U, wherein the second carrier comprises a fourth adhesive layer coated thereon, wherein the second dry component is adhered to the fourth adhesive layer.

Embodiment W is the device of any one of the preceding Embodiments, wherein the base further comprises a first tab proximate the opening.

Embodiment X is the device of Embodiment W, wherein the first tab comprises a first closure adhesive adhered thereto.

Embodiment Y is the device of Embodiment X, further comprising a first release liner releasably adhered to the first closure adhesive.

Embodiment Z is the device of any one of the preceding Embodiments, wherein the coversheet further comprises a second tab proximate the opening.

Embodiment AA is the device of Embodiment Z, wherein the second tab comprises a second closure adhesive adhered thereto.

Embodiment AB is the device of Embodiment AA, further comprising a second release liner releasably adhered to the second closure adhesive.

Embodiment AC is a device, comprising:
a body comprising a planar waterproof substrate comprising:
a peripheral edge:
a first major surface comprising spaced-apart first and second sections;
a second major surface opposite the first major surface;
a fold that places a first section in overlapping juxtaposition with respect to the second section;
wherein the first section and the second section define inner walls of a growth compartment that comprises a perimeter and an opening that provides liquid access to the growth compartment;
wherein a portion of the perimeter is defined by a waterproof seal, wherein the portion includes >50% of the perimeter;
a cold water-soluble gelling agent adhered to the first section in the growth compartment;
a dry culture medium disposed in the growth compartment, the culture medium selected to facilitate growth of a sulfate-reducing bacterium; or an indicator reagent for detecting hydrogen sulfide production by a sulfate-reducing bacterium, wherein the indicator reagent is disposed in the growth compartment; and
a dry first oxygen-scavenging reagent disposed in the growth compartment.

Embodiment AD is the device of Embodiment AC, wherein the body is substantially two-dimensional.

Embodiment AE is the device of Embodiment AC or Embodiment AD, further comprising a dry reducing agent disposed in the growth compartment.

Embodiment AF is the device of any one of Embodiments AC through AE, wherein the culture medium comprises an organic carbon source.

Embodiment AG is the device of Embodiment AF, wherein the organic carbon source is nonfermentable.

Embodiment AH is the device of any one of Embodiments AC through AG, further comprising a dry second oxygen-scavenging reagent disposed in the growth compartment.

Embodiment AI is the device of any one of Embodiments AC through AH, wherein the device comprises the culture medium and the indicator reagent, wherein the culture medium and the indicator reagent are both disposed in the growth compartment.

Embodiment AJ is the device of any one of Embodiments AC through AI, wherein a first dry component selected from the group consisting of the first oxygen-scavenging reagent, the second oxygen-scavenging reagent, the reducing reagent, the culture medium, the indicator reagent and a combination of any two or more of the foregoing components is adhered to the first section of the planar waterproof substrate.

Embodiment AK is the device of Embodiment AJ, wherein the planar waterproof substrate comprises a first adhesive layer disposed on at least a portion of the first section, wherein the first dry component is adhered to the first adhesive layer in the growth compartment.

Embodiment AL is the device of Embodiment AJ, further comprising a first carrier, wherein the first dry component is adhered to the first carrier, wherein the first carrier is adhered to the first adhesive layer in the growth compartment.

Embodiment AM is the device of Embodiment AL, wherein the first carrier comprises a second adhesive layer coated thereon, wherein the first dry component is adhered to the second adhesive layer.

Embodiment AN is the device of any one of Embodiments AC through AM, wherein a second dry component selected from the group consisting of the first oxygen-scavenging reagent, the second oxygen-scavenging reagent, the reducing reagent, the culture medium, the indicator reagent and a combination of any two or more of the foregoing components is adhered to the second section of the planar waterproof substrate.

Embodiment AO is the device of Embodiment AN:
wherein the waterproof substrate comprises a third adhesive layer disposed on at least a portion of the second section;
wherein the second dry component is adhered to the third adhesive layer in the growth compartment.

Embodiment AP is the device of Embodiment AN, further comprising a second carrier, wherein the second dry component is adhered to a second carrier, wherein the second carrier is adhered to the second adhesive layer in the growth compartment.

Embodiment AQ is the device of Embodiment AP, wherein the second carrier comprises a fourth adhesive layer coated thereon, wherein the second dry component is adhered to the fourth adhesive layer.

Embodiment AR is the device of any one of the preceding Embodiments, wherein the portion includes at least 80% of the perimeter.

Embodiment AS is the device of Embodiment AR, wherein the portion includes at least 90% of the perimeter.

Embodiment AT is the device of Embodiment AS, wherein the portion includes at least 95% of the perimeter.

Embodiment AU is the device of Embodiment AT, wherein the portion includes 100% of the perimeter.

Embodiment AV is the device of any one of the preceding Embodiments, wherein the cold water-soluble gelling agent is selected from the group consisting of hydroxypropyl methylcellulose, xanthan gum, guar gum, locust bean gum, carboxymethyl cellulose, hydroxyethyl cellulose, algin, and combinations thereof.

Embodiment AW is the device of any one of the preceding Embodiments, wherein the first oxygen-scavenging reagent is water-soluble.

Embodiment AX is the device of any one of the preceding Embodiments, wherein the first oxygen-scavenging reagent is selected from the group consisting of ferric ammonium sulfate, ferric chloride, a ferric iron salt, a sulfite salt, and a bisulfite salt.

Embodiment AY is the device of Embodiment L or Embodiment AH, wherein the second oxygen-scavenging reagent is water-soluble Embodiment AZ is the device of Embodiment AY, wherein the second oxygen-scavenging reagent is selected from the group consisting of ascorbic acid and salts thereof, and an enzyme capable of catalyzing a reaction that consumes molecular oxygen.

Embodiment BA is the device of Embodiment F or Embodiment AE, wherein the reducing agent is selected from the group consisting of dithiothreitol, dithioerythritol, a salt of thioglycolic acid, and a combination of any two or more of the foregoing.

Embodiment BB is the device of any one of the preceding Embodiments, any one of the preceding claims, wherein the waterproof seal comprises an adhesive.

Embodiment BC is the device of Embodiment BB, wherein the adhesive comprises a pressure-sensitive adhesive.

Embodiment BD is a method, comprising:
depositing a sample into a growth compartment of a device, the device comprising:
 a body comprising the growth compartment disposed between a waterproof base and a waterproof coversheet attached to the base, the growth compartment having a perimeter and an opening that provides liquid access to the growth compartment;
  wherein a portion of the perimeter is defined by a waterproof seal,
 wherein the portion includes >50% of the perimeter;
 a dry cold water-soluble gelling agent adhered to the base in the growth compartment; and
 a dry first oxygen-scavenging reagent disposed in the growth compartment;
incubating the device at a temperature that facilitates growth of a sulfate-reducing microorganism; and
detecting an indication of a colony of the sulfate-reducing microorganism in the growth compartment.

Embodiment BE is a method, comprising:
depositing a sample into a growth compartment of a device, the device comprising:
 a body comprising a planar waterproof substrate comprising:
 a peripheral edge:
 a first major surface comprising spaced-apart first and second sections;
 a second major surface opposite the first major surface;
 a fold that places a first section in overlapping juxtaposition with respect to the second section;
  wherein the first section and the second section define inner walls of a growth compartment that comprises a perimeter and an opening that provides liquid access to the growth compartment;
  wherein a portion of the perimeter is defined by a waterproof seal, wherein the portion includes >50% of the perimeter;
 a cold water-soluble gelling agent adhered to the first section in the growth compartment; and
 a dry first oxygen-scavenging reagent disposed in the growth compartment and
incubating the device at a temperature that facilitates growth of a sulfate-reducing microorganism; and
detecting an indication of a colony of the sulfate-reducing microorganism in the growth compartment.

Embodiment BF is the method of Embodiment BD or Embodiment BE wherein, prior to depositing the sample into the growth compartment, the growth compartment contains a dry culture medium, the culture medium selected to facilitate growth of a sulfate-reducing bacterium.

Embodiment BG is the method of any one of Embodiments BC through BF wherein, prior to depositing the sample into the growth compartment, the growth compartment contains an indicator reagent for detecting hydrogen sulfide production by a sulfate-reducing bacterium.

Embodiment BH is the method of any one of Embodiments BC through BG, wherein depositing the sample into the growth compartment further comprises depositing an aqueous liquid into the growth compartment.

Embodiment BI is the method of Embodiment BH, wherein the sample is disposed in the aqueous liquid.

Embodiment BJ is the method of Embodiment BH or Embodiment BI, wherein depositing the aqueous liquid into the growth compartment comprises depositing a predetermined volume of the aqueous liquid.

Embodiment BK is the method of Embodiment BJ, wherein depositing a predetermined volume comprises depositing about 0.1 mL to about 100 mL.

Embodiment BL is the method of any one of Embodiments BC through BK, wherein the method further comprises sealing the opening.

Embodiment BM is the method of any one of Embodiments BC through BL, wherein incubating the device includes incubating the device for a period 7 days or less.

Embodiment BN is the method of Embodiment BM, wherein incubating the device includes incubating the device for a period 96 hours or less.

Embodiment BO is the method of Embodiment BN, wherein incubating the device includes incubating the device for a period 72 hours or less.

Embodiment BP is the method of Embodiment BO, wherein incubating the device includes incubating the device for a period 48 hours or less.

Embodiment BQ is the method of Embodiment BP, wherein incubating the device includes incubating the device for a period 24 hours or less.

Objects and advantages of this invention are further illustrated by the following examples, but the particular materials and amounts thereof recited in these examples, as well as other conditions and details, should not be construed to unduly limit this invention.

EXAMPLES

Example 1: Device Construction (Pattern Coated, Single Sided)

75 μm (3.0 mil) polyethylene terephthalate (PET) film (Melanex 454, Tekra, New Berlin, Wis.) was coated with an isooctyl acrylate/acrylamide pressure sensitive adhesive (PSA) described in Example 1 of U.S. Pat. No. 5,409,838. A silicone coated paper release liner (D #63 BL KFT H/O 548440/000; Loprex GmbH, Stuttgart, Germany) with a 7.62 cm by 10.16 cm (3 inch by 4 inch) square removed from the middle was used to mask the adhesive boarder. Exposed adhesive was powder coated with various mixtures of cold water soluble gelling agents and oxygen scavengers/reducing agents (Table 1). The powder was evenly applied and excess powder was removed from the adhesive layer by hand shaking of the film followed by removal of the release liner. A strip of silicone coated paper release liner was adhered to the adhesive above one of the 7.62 cm (3 inch) sides of the powder coated portion of the film. A piece of 125 μm (5 mil) PET film (Melanex 454, Tekra, New Berlin, Wis.) was then laminated to the remaining exposed adhesive forming a pouch with a release liner preventing sealing at one end.

Example 2: Device Construction (Pattern Coated, Double Sided)

75 μm (3.0 mil) mil polyethylene terephthalate (PET) film (Melanex 454, Tekra, New Berlin, Wis.) was coated with an isooctyl acrylate/acrylamide pressure sensitive adhesive (PSA) described in Example 1 of U.S. Pat. No. 5,409,838. A silicone coated paper release liner with a 7.62 cm by 10.16 cm (3 inch by 4 inch) square removed from the middle was used to mask the adhesive boarder. Exposed adhesive was powder coated with various mixtures of cold water soluble gelling agents and oxygen scavengers/reducing agents (Table 1). The powder was evenly applied and excess powder was removed from the adhesive layer by hand shaking of the film followed by removal of the release liner. A strip of silicone coated paper release liner was adhered to the adhesive above one of the 7.62 cm (3 inch) sides of the powder coated portion of the film. Two powder coated films with adhered release liners were made in this fashion and laminated together with the powder coated portions facing in and overlapping and the adhered release liners overlapping as well (See FIG. 2).

Example 3: Device Construction (Powder Coated Carrier Substrate, Single Sided)

75 μm (3.0 mil) polyethylene terephthalate (PET) film (Melanex 454, Tekra, New Berlin, Wis.) was coated with an isooctyl acrylate/acrylamide pressure sensitive adhesive (PSA) described in Example 1 of U.S. Pat. No. 5,409,838. The adhesive was powder coated with various mixtures of cold water soluble gelling agents and oxygen scavengers/reducing agents (Table 1). The powder was evenly applied and excess powder was removed from the adhesive layer by hand shaking of the film. The powder coated film was cut into a 7.62 cm by 10.16 cm (3 inch by 4 inch) rectangle and placed in the center of a 10.16 cm by 12.7 cm (4 inch by 5 inch) piece of adhesive coated PET. A strip of silicone coated paper release liner was adhered to the adhesive coated film above one of the 7.62 cm (3 inch) sides of the powder coated carrier film. A piece of 125 μm (5 mil) PET film (Melanex 454, Tekra, New Berlin, Wis.) was then laminated to the remaining exposed adhesive forming a pouch with a release liner preventing sealing at one end.

Example 4: Device Construction (Powder Coated Carrier Substrate, Double Sided)

75 μm (3.0 mil) polyethylene terephthalate (PET) film (Melanex 454, Tekra, New Berlin, Wis.) was coated with an isooctyl acrylate/acrylamide pressure sensitive adhesive (PSA) described in Example 1 of U.S. Pat. No. 5,409,838. The adhesive was powder coated with various mixtures of cold water soluble gelling agents and oxygen scavengers/reducing agents (Table 1). The powder was evenly applied and excess powder was removed from the adhesive layer by hand shaking of the film. The powder coated film was cut into a 7.62 cm by 10.16 cm (3 inch by 4 inch) rectangle and placed in the center of a 10.16 cm by 12.7 cm (4 inch by 5 inch) piece of adhesive coated PET. A strip of silicone coated paper release liner was adhered to the adhesive coated film above one of the 7.62 cm (3 inch) sides of the powder coated carrier film. Two constructions were made in this fashion and laminated together with the powder coated carrier films facing in and overlapping and the adhered release liners overlapping as well (See FIG. 5).

Example 5: Device Construction (One Powder and One Broth Coated Carrier, Double Sided)

Part one of the construction was made by coating a 75 μm (3.0 mil) polyethylene terephthalate (PET) film (Melanex 454, Tekra, New Berlin, Wis.) with an isooctyl acrylate/acrylamide pressure sensitive adhesive (PSA) described in Example 1 of U.S. Pat. No. 5,409,838. The adhesive was powder coated with various mixtures of cold water soluble gelling agents and oxygen scavengers/reducing agents (Table 1). The powder was evenly applied and excess powder was removed from the adhesive layer by hand shaking of the film. The powder coated film was cut into a 7.62 cm by 10.16 cm (3 inch by 4 inch) rectangle and placed in the center of a 10.16 cm by 12.7 cm (4 inch by 5 inch) piece of adhesive coated PET. A strip of silicone coated paper release liner was adhered to the adhesive coated film above one of the 7.62 cm (3 inch) sides of the powder coated carrier film.

Part two of the construction was made by coating 75 μm (3.0 mil) polyethylene terephthalate (PET) film (Melanex 454, Tekra, New Berlin, Wis.) with a medium formulation (BD Bacto Tryptone 10 g/L (Becton Dickinson Corp, New Franklin, N.J.), Amresco Soytone 10 g/L (Amresco, Solon, Ohio), BD Bacto Yeast 2 g/L (Becton Dickinson Corp, New Franklin, N.J.), $MgSO_4·7H_2O$ 4 g/L (EMD Millipore, Billerica, Mass.), 60% Sodium Lactate Syrup 8 mls/L (Sigma Aldrich Co., St. Louis, Mo.), Sodium Acetate 5 g/L (Sigma Aldrich Co., St. Louis, Mo.), NaCl 10 g/L (EMD Millipore, Billerica, Mass.), NH$_4$Cl 0.2 g/L (JT Baker, Center Valley, Pa.), M150 Guar 8 g/L, pH to 7.3 with NaOH, mixed under high shear) at 300 μm (12.0 mil) thick followed by 10 minutes at 180° C. in a solvent oven. A 7.62 cm by 10.16 cm (3 inch by 4 inch) piece of the broth coated PET was cut and placed in the center of a 10.16 cm by 12.7 cm (4 inch by 5 inch) piece of adhesive coated PET. A strip of silicone coated paper release liner was adhered to the adhesive coated film above one of the 7.62 cm (3 inch) sides of the broth coated carrier film.

Part one and Part two of the construction were laminated powder coat in to broth coat in with the adhered release liners overlapping as well (See FIG. 5). This resulted in a pouch construction with an internal microbial growth compartment with opposing powder and broth coated sides kept open on one side by release liners.

Example 6: Growth and Maintenance of Sulfate Reducing Bacterial Stock Cultures

Stock cultures of SRBs *Desulfovibrio desulfuricans* (ATCC #29577; American Type Culture Collection, Manassas, Va.) and *Desulfovibrio vulgaris* (ATCC #29579; American Type Culture Collection, Manassas, Va.) were grown and maintained in a modified sodium lactate medium (Yeast Extract 1 g (Becton Dickinson Corp, New Franklin, N.J.), MgSO$_4$-7H$_2$O 1 g (EMD Millipore, Billerica, Mass.), NH$_4$Cl 0.4 g (JT Baker, Center Valley, Pa.), K$_2$HPO$_4$ 0.01 g (MP Biochemicals LLC, Solon, Ohio), NaCl 5 g (EMD Millipore, Billerica, Mass.), sodium ascorbate 0.1 g (Sigma Aldrich Co., St. Louis, Mo.), sodium lactate (60%) 4 mls (Sigma Aldrich Co., St. Louis, Mo.), pH to 7.3 with NaOH (Sigma Aldrich Co., St. Louis, Mo.) tubed immediately after autoclaving under a 97% nitrogen/3% hydrogen atmosphere in Balch tubes using butyl rubber stoppers and aluminum crimps. Cultures were passaged weekly by back diluting 1/100 into a tube of the modified sodium lactate medium using gassed 1 ml syringes. Cultures were incubated for 48 hours at 30° C. and then kept at 4° C. for an additional 5 days. After the 6$^{th}$ passage, cultures were thrown out and freshly inoculated from freezer stocks.

Example 7: Inoculation of Devices

The devices of Examples 1-5 were inoculated as follows. Samples (either 5 or 10 mls) were placed in the devices either by directly pouring them in or using a 10 ml sterile pipette. The release liners were removed and the devices were slid between two parallel Plexiglas plates in order to push the sample to the top of the growth zone and exclude air. The now exposed PSA at the mouth of the device was pressed together to form a seal and the devices were laid flat for incubation. Incubation was performed at 30° C. for up to 10 day to allow time for bacterial growth. Colonies were visualized as small black spots resulting from the formation of insoluble iron sulfide precipitate from the combination of bacterial hydrogen sulfide production and iron present in the medium.

Example 8: Growth of Sulfate Reducing Bacteria Using Ascorbate in a Double Sided Powder Construction The devices of Example 4 were constructed using the powder coating mixtures 1-9 from Table 1. Stock cultures of *Desulfovibrio desulfuricans* (ATCC #29577) and *Desulfovibrio vulgaris* (ATCC #29579) from Example 6 were serially diluted in aerobic medium described in Table 2. An amount of 5 mls of the 10$^{-6}$ dilution was inoculated and the devices were incubated as described in detail in Example 7. After 96 hours the devices were examined for growth of SRBs with the results reported in Table 3.

Example 9: Growth of Sulfate Reducing Bacteria Using Ferrous Iron in a Double Sided Powder Construction The devices of Example 4 were constructed using the powder coating mixtures 1 and 10-12 from Table 1. Stock cultures of *Desulfovibrio vulgaris* (ATCC #29579) from Example 6 were serially diluted in aerobic medium described in Table 4. An amount of 5 mls of the 10$^{-5}$ dilution was inoculated and the devices were incubated as described in detail in Example 7. After 72 hours the devices were examined for growth of SRBs with the results reported in Table 3.

Example 10: Device Construction with Alternative Carrier Web Shape

The Devices in Example 3 were constructed with an alternative carrier web shape shown in FIG. 3.

Example 11: Device Construction with Alternative Carrier Web Shape

The Devices in Example 4 were constructed with an alternative carrier web shape shown in FIG. 3.

Example 12: Device Construction with Alternative Carrier Web Shape

The Devices in Examples 5 were constructed with an alternative carrier web shape shown in FIG. 3.

Example 13: Growth of Sulfate Reducing Bacteria Using Ferrous Iron in a Double Sided Powder/Broth Construction The devices of Example 5 were constructed using the powder coating mixture 11 from Table 1. Stock cultures of *Desulfovibrio vulgaris* (ATCC #29579) from Example 6 were serially diluted in phosphate buffered saline (Sigma). An amount of 5 mls of the 10$^{-5}$, 10$^{-6}$, and 10$^{-7}$ dilution were inoculated and the devices were incubated as described in detail in Example 7. After 120 hours the devices were examined for growth of SRBs with the results reported in Table 3.

Example 14: Growth of Sulfate Reducing Bacteria Using Differing Gel Strength

The devices of Example 3 were constructed using the powder coating mixture 2 from Table 1. Stock cultures of *Desulfovibrio desulfuricans* (ATCC #29577) and *Desulfovibrio vulgaris* (ATCC #29579) from Example 6 were serially diluted in aerobic medium described in Table 2. An amount of 2, 3, 4, or 5 mls of the 10$^{-7}$ dilution was inoculated and the devices were incubated as described in detail in Example 7. After 72 hours the devices were examined for growth of SRBs with the results reported in Table 5.

Comparative Example 1: Construction of a Total Count Thin-Film Culture Device 75 μm (3.0 mil) polyethylene terephthalate (PET) film (Melanex 454, Tekra, New Berlin, Wis.) was coated with an isooctyl acrylate/acrylamide pressure sensitive adhesive (PSA) described in Example 1 of U.S. Pat. No. 5,409,838. The adhesive was powder coated with mixture 2 from Table 1. The powder was evenly applied and excess powder was removed from the adhesive layer by hand shaking of the film. The powder coated film was cut into 7.62 cm by 10.16 cm (3 inch by 4 inch) rectangles. Two rectangles were joined along one 7.62 cm (3 inch) side using two-sided tape powder sides facing in.

Comparative Example 2: Construction of a Thin Film Culture Device with a Spacer 75 μm (3.0 mil) polyethylene terephthalate (PET) film (Melanex 454, Tekra, New Berlin, Wis.) was coated with an isooctyl acrylate/acrylamide pressure sensitive adhesive (PSA) described in Example 1 of U.S. Pat. No. 5,409,838. The adhesive was powder coated with mixture 2 from Table 1. The powder was evenly applied and excess powder was removed from the adhesive layer by hand shaking of the film. The powder coated film was cut into 7.62 cm by 10.16 cm (3 inch by 4 inch) rectangles.

100 μm (4 mil) mil polyethylene terephthalate (PET) film (LAB plate bottom film?) was coated with an isooctyl acrylate/acrylamide pressure sensitive adhesive (PSA) described in Example 1 of U.S. Pat. No. 5,409,838. A silicone coated paper release liner with a 6 centimeter diameter circle removed was used to mask the adhesive. Exposed adhesive was powder coated with mixture 2 from Table 1. The powder was evenly applied and excess powder was removed from the adhesive layer by hand shaking of the film followed by removal of the release liner. A foam spacer (polystyrene foam; 76 mm wide by 102 mm long by 0.57 mm thick) with a circular opening 61 mm in diameter was adhesively laminated to the adhesive coated side of the first layer. The powder coated film with adhered spacer was cut into 7.62 cm by 10.16 cm (3 inch by 4 inch) rectangles.

The two films described above were joined along one 7.62 cm (3 inch) side using two-sided tape powder sides facing in.

Comparative Example 3: Growth of SRBs in Thin Film Culture Devices

The devices of Comparative Example 1 were constructed and stock cultures of *Desulfovibrio desulfuricans* (ATCC #29577) from Example 6 were serially diluted in aerobic medium described in Table 2 to which ascorbate oxidase (Calzyme Laboratories, San Luis Obispo, Calif.) was added to a final concentration of 4 U/ml. 3 mls of the $10^{-5}$, $10^{-6}$, and $10^{-7}$ dilutions were inoculated by lifting up the top film, dispensing the sample in the middle of the bottom film, and gently placing the top film back down. Plates were incubated at 30° C. either in ambient atmosphere or in an anaerobic chamber purged with a 97% $N_2$ 3% $H_2$ gas. After 72 hours the devices were examined for growth of SRBs with the results reported in Table 6.

Comparative Example 4: Growth of SRBs in Thin Film Culture Devices

The devices of Comparative Example 2 were constructed and stock cultures of *Desulfovibrio desulfuricans* (ATCC #29577) from Example 6 were serially diluted in aerobic medium described in Table 2 to which ascorbate oxidase (Calzyme Laboratories, San Luis Obispo, Calif.) was added to a final concentration of 4 U/ml. An amount of 3 mls of the $10^{-5}$, $10^{-6}$, and $10^{-7}$ dilutions were inoculated by lifting up the top film, dispensing the sample in the middle of the bottom film, and gently placing the top film back down. Plates were incubated at 30° C. either in ambient atmosphere or in an anaerobic chamber purged with a 97% $N_2$ 3% $H_2$ gas. After 72 hours the devices were examined for growth of SRBs with the results reported in Table 6.

Example 15: Construction and Use of Pouch-Like Culture Devices

The devices of Example 3 were constructed with except the backing film was 48 ga PET/98 ga WOPP/0.00035" Foil/2 mil Barex (Technipaq, Crystal Lake, Ill.) instead of 75 μm (3 mil) PET and the powder coating mixture as follows; M150 Guar 5 g (DuPont Danisco, Copenhagen, Denmark), Fortefiber HB Ultra 89.3 g (Dow Chemical Company, Midland, Mich.), FeSO4-7H20 3 g (JT Baker, Center Valley, Pa.), sodium ascorbate 0.60 g (Sigma Aldrich Co., St. Louis, Mo.), sodium thioglycolate: 1.5 g (Sigma Aldrich Co., St. Louis, Mo.), CaSO4: 0.60 g (JT Baker, Center Valley, Pa.). FeSO4-7H20 and Sodium Ascorbate were milled as in Table 1. Stock cultures of *Desulfovibrio desulfuricans* (ATCC #29577) and *Desulfovibrio vulgaris* (ATCC #29579) from Example 6 were serially diluted in aerobic medium; $K_2HPO_4$ 0.56 g/L (MP Biochemicals LLC, Solon, Ohio), $KH_2PO_4$ 0.11 g/L (MP Biochemicals LLC, Solon, Ohio), $NH_4Cl$ 1.0 g/L (JT Baker, Center Valley, Pa.), $MgSO_4\text{-}7H_2O$ 3.0 g/L (EMD Millipore, Billerica, Mass.), 60% Na Lactate 4.0 mL/L (Sigma Aldrich Co., St. Louis, Mo.), Bacto Yeast Extract 1.0 g/L (Becton Dickinson Corp, New Franklin, N.J.), Bacto Tryptone 1 g/L (Becton Dickinson Corp, New Franklin, N.J.), Resazurin: 1 mg/L (MP Biochemicals LLC, Solon, Ohio), ATCC Vitamin Mix 10 mL/L (American Type Culture Collection, Manassas, Va.), ATCC Trace Mineral Mix 10 mL/L. pH was adjusted to 7.3 with sodium hydroxide and filter sterilized. An amount of 5 mls of the $10^{-6}$ and $10^{-7}$ dilutions were inoculated and the devices were incubated as described in detail in Example 7. After 96 hours the devices were examined for growth of SRBs. Both strain grew well with single colonies being easily counted at this time.

TABLE 1

Powder coat formulations. All values are represented in grams. $C_6H_7NaO_6$ (Sigma Aldrich Co., St. Louis, MO), and $FeSO_4\text{—}7H_2O$ (JT Baker, Center Valley, PA) were obtained in crystal form and milled to an average particle size of <100 μm prior to mixing and powder coating. HPMC (hydroxypropyl methylcellulose; Fortefiber HB Ultra) was obtained from Dow Chemical Company (Midland, MI).

|   | HPMC | $C_6H_7NaO_6$ | $FeSO_4\text{—}7H_2O$ |
|---|------|---------------|------------------------|
| 1 | 100 | — | — |
| 2 | 100 | 10.00 | — |
| 3 | 100 | 5.000 | — |
| 4 | 100 | 2.500 | — |
| 5 | 100 | 1.250 | — |
| 6 | 100 | 0.625 | — |
| 7 | 100 | 0.313 | — |
| 8 | 100 | 0.156 | — |
| 9 | 100 | 0.078 | — |
| 10 | 100 | — | 5.00 |
| 11 | 100 | — | 2.50 |
| 12 | 100 | — | 1.25 |

TABLE 2

SRB Medium Formulation. The pH was adjusted to 7.3 with sodium hydroxide and filter sterilized.

| Component | Amount (g/L) | Source |
|---|---|---|
| Enzymatic digest of casein (Tryptone) | 5 | Becton Dickinson Corp, New Franklin, NJ |
| Enzymatic digest of soy (Soytone) | 5 | Amresco, Solon, OH |
| Yeast extract | 1 | Becton Dickinson Corp, New Franklin, NJ |
| Magnesium sulfate heptahydrate | 2.0 | EMD Millipore, Billerica, MA |
| Sodium chloride | 5.0 | EMD Millipore, Billerica, MA |
| Sodium lactate | 2.5 | EMD Millipore, Billerica, MA |
| Ferrous Ammonium Sulfate | 0.5 | EMD Millipore, Billerica, MA |

TABLE 3

Growth of SRBs in devices using ascorbate or ferrous iron. Where multiple dilutions of SRB were inoculated for a given device the dilution is indicated in parentheses.

| Example | Powder Mixture | D. vulgaris | D. desulfuricans |
|---|---|---|---|
| 8 | 1 | +++ | +++ |
| 8 | 2 | +++ | +++ |
| 8 | 3 | +++ | +++ |
| 8 | 4 | +++ | +++ |
| 8 | 5 | +++ | +++ |
| 8 | 6 | +++ | +++ |
| 8 | 7 | +++ | +++ |
| 8 | 8 | ++ | ++ |
| 8 | 9 | − | + |
| 9 | 1 | − | − |
| 9 | 10 | +++ | +++ |
| 9 | 11 | +++ | +++ |
| 9 | 12 | +++ | +++ |
| 13 | 11 | TNTC ($10^{-5}$) | ND |
| 13 | 11 | +++ ($10^{-6}$) | ND |
| 13 | 11 | +++ ($10^{-7}$) | ND |

+++ = Luxuriant growth throughout plate, single colonies easily countable
++ = Growth present with some inhibition around the edges of the plate, single colonies countable
+ = Growth present with marked inhibition around edges of the plate, colonies difficult to distinguish
− = No black precipitate observed
TNTC = Too numerous to count.
ND = Not determined

TABLE 4

SRB Medium Formulation. The pH was adjusted to 7.3 with sodium hydroxide and filter sterilized.

| Component | Amount (g/L) | Source |
|---|---|---|
| Enzymatic digest of casein (Tryptone) | 10 | Becton Dickinson Corp, New Franklin, NJ |
| Yeast extract | 1 | Becton Dickinson Corp, New Franklin, NJ |
| Potassium phosphate, monobasic | 0.2 | MP Biochemicals LLC, Solon, OH |
| Ammonium chloride | 0.053 | JT Baker, Center Valley, PA |
| Magnesium sulfate heptahydrate | 2.0 | EMD Millipore, Billerica, MA |
| Sodium chloride | 5.0 | EMD Millipore, Billerica, MA |
| Sodium lactate | 2.5 | Sigma Aldrich Co., St. Louis, MO |

TABLE 5

Growth of SRBs in devices with varying gel strengths.

| Inoculum Volume (ml) | D. vulgaris | D. desulfuricans |
|---|---|---|
| 2 | + | − |
| 3 | ++ | + |
| 4 | +++ | +++ |
| 5 | +++ | +++ |

+++ = Luxuriant growth throughout plate, single colonies easily countable
++ = Growth present with some inhibition around the edges of the plate, single colonies countable
+ = Growth present with marked inhibition around edges of the plate, colonies difficult to distinguish
− = No black precipitate observed

TABLE 6

Growth of SRBs in traditional thin-film culture device constructions.

| Example | Atmosphere | Dilution | Growth |
|---|---|---|---|
| 17 | Ambient | $10^{-4}$ | − |
| 17 | Ambient | $10^{-5}$ | − |
| 17 | Ambient | $10^{-6}$ | − |
| 17 | Anaerobic | $10^{-4}$ | +++ |
| 17 | Anaerobic | $10^{-5}$ | +++ |
| 17 | Anaerobic | $10^{-6}$ | +++ |
| 18 | Ambient | $10^{-4}$ | ++ |
| 18 | Ambient | $10^{-5}$ | + |
| 18 | Ambient | $10^{-6}$ | − |
| 18 | Anaerobic | $10^{-4}$ | +++ |
| 18 | Anaerobic | $10^{-5}$ | +++ |
| 18 | Anaerobic | $10^{-6}$ | +++ |

+++ = Luxuriant growth throughout plate, single colonies easily countable
++ = Growth present with some inhibition around the edges of the plate, single colonies not countable
+ = Growth present with marked inhibition around edges of the plate, colonies difficult to distinguish
− = No black precipitate observed The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

What is claimed is:

1. A device, comprising:
a body comprising a waterproof base, a waterproof coversheet attached to the base, and a growth compartment disposed therebetween, the growth compartment having a perimeter and an opening that provides liquid access to the growth compartment;
wherein a first portion of the perimeter is defined by a waterproof seal, wherein the first portion includes >50% of the perimeter, and wherein a second portion of the perimeter is defined by the opening that provides liquid access to the growth compartment;

a dry cold water-soluble gelling agent adhered to the base in the growth compartment;

an indicator reagent for detecting hydrogen sulfide production by a sulfate-reducing bacterium, wherein the indicator reagent is disposed in the growth compartment; and a dry first oxygen-scavenging reagent disposed in the growth compartment.

2. The device of claim 1, further comprising a dry culture medium disposed in the growth compartment, the dry culture medium selected to facilitate growth of a sulfate-reducing bacterium.

3. The culture device of claim 1, further comprising an effective amount of a dry reducing agent disposed in the growth compartment.

4. The device of claim 3, wherein the reducing agent is selected from the group consisting of dithiothreitol, dithioerythritol, a salt of thioglycolic acid, and a combination of any two or more of the foregoing.

5. The device of claim 1, wherein the dry first oxygen-scavenging reagent is adhered to the base.

6. The device of claim 1, further comprising an indicator reagent for detecting a presence of a viable microorganism, wherein the indicator reagent is disposed in the growth compartment.

7. The device of claim 6, wherein the indicator reagent for detecting a presence of a viable microorganism is the dry first oxygen-scavenging reagent or a dry second oxygen-scavenging reagent.

8. The device of claim 1, further comprising a dry second oxygen-scavenging reagent disposed in the growth compartment.

9. The device of claim 1, wherein a dry component selected from the group consisting of the dry first oxygen-scavenging reagent, a second oxygen-scavenging reagent, a reducing reagent, a culture medium selected to facilitate growth of a sulfate-reducing bacterium, the indicator reagent for detecting hydrogen sulfide production by a sulfate-reducing bacterium, and a combination of any two or more of the foregoing components is adhered to the base.

10. The device of claim 1, wherein a dry component selected from the group consisting of the dry first oxygen-scavenging reagent, a second oxygen-scavenging reagent, a reducing reagent, a culture medium selected to facilitate growth of a sulfate-reducing bacterium, the indicator reagent for detecting hydrogen sulfide production by a sulfate-reducing bacterium, and a combination of any two or more of the foregoing components is adhered to the coversheet.

11. The device of claim 1, further comprising a carrier, wherein the dry cold water-soluble gelling agent, the indicator reagent for detecting hydrogen sulfide production by a sulfate-reducing bacterium, the dry first oxygen-scavenging reagent, or a combination thereof is adhered to the carrier, and wherein the carrier is adhered to the base.

12. The device of claim 1, further comprising a tab releasably adhered to the base proximate the opening, wherein the tab comprises a release coating applied thereto.

13. The device of claim 1, wherein the dry cold water-soluble gelling agent is selected from the group consisting of hydroxypropyl methylcellulose, xanthan gum, guar gum, locust bean gum, carboxymethyl cellulose, hydroxyethyl cellulose, algin, and combinations thereof.

14. The device of claim 1, wherein the dry first oxygen-scavenging reagent is selected from the group consisting of ferric ammonium sulfate, ferric chloride, ferric iron salts, sulfite salts, bisulfite salts.

15. The device of claim 1, wherein the waterproof seal comprises an adhesive.

16. A method, comprising:
depositing a sample into a growth compartment of a device, the device comprising:
a body comprising the growth compartment disposed between a waterproof base and a waterproof coversheet attached to the base, the growth compartment having a perimeter and an opening that provides liquid access to the growth compartment;
wherein a first portion of the perimeter is defined by a waterproof seal, wherein the first portion includes >50% of the perimeter, and wherein a second portion of the perimeter is defined by the opening that provides liquid access to the growth compartment;
a dry cold water-soluble gelling agent adhered to the base in the growth compartment; and
a dry first oxygen-scavenging reagent disposed in the growth compartment;
incubating the device at a temperature that facilitates growth of a sulfate-reducing microorganism; and
detecting an indication of a colony of the sulfate-reducing microorganism in the growth compartment.

17. The method of claim 16 wherein, prior to depositing the sample into the growth compartment, the growth compartment contains a dry culture medium, the dry culture medium selected to facilitate growth of a sulfate-reducing bacterium.

18. The method of claim 16, wherein depositing the sample into the growth compartment further comprises depositing an aqueous liquid into the growth compartment.

19. The method of claim 16, wherein the method further comprises sealing the opening.

20. The method of claim 16, wherein incubating the device includes incubating the device for a period 7 days or less.

* * * * *

UNITED STATES PATENT AND TRADEMARK OFFICE
CERTIFICATE OF CORRECTION

PATENT NO. : 10,808,215 B2
APPLICATION NO. : 15/503481
DATED : October 20, 2020
INVENTOR(S) : Brutinel et al.

It is certified that error appears in the above-identified patent and that said Letters Patent is hereby corrected as shown below:

On the Title Page

Column 2, item (56) Under (Other Publications)
Line 6, delete "Federaiont);" and insert -- Federation); --, therefor.

In the Specification

Column 12
Line 61, delete "an" and insert -- and --, therefor.

Column 17
Line 4, delete "know" and insert -- known --, therefor.
Line 8, delete "know" and insert -- known --, therefor.

Column 18
Line 44, delete "4c" and insert -- 11C --, therefor.

Column 22
Line 43, delete "bromcresol" and insert -- bromocresol --, therefor.
Line 47, delete "bromcresol" and insert -- bromocresol --, therefor.

Column 27
Line 36, after "water-soluble" insert -- . --.

Column 28
Line 61, after "period" insert -- of --.
Line 64, after "period" insert -- of --.
Line 67, after "period" insert -- of --.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*

Column 29
Line 3, after "period" insert -- of --.
Line 6, after "period" insert -- of --.

Column 34
Line 23, delete "FeSO4-7H20" and insert -- $FeSO_4$-$7H_2O$ --, therefor.
Line 27, delete "FeSO4-7H20" and insert -- $FeSO_4$-$7H_2O$ --, therefor.

In the Claims

Column 37
Line 13, in Claim 3, before "device" delete "culture".

Column 38
Line 50, in Claim 20, after "period" insert -- of --.